(12) United States Patent
Quarre et al.

(10) Patent No.: US 9,227,188 B2
(45) Date of Patent: Jan. 5, 2016

(54) DEVICE, SYSTEM, AND METHOD FOR SELECTING A TARGET ANALYTE OR FLUID

(71) Applicant: RareCyte, Inc., Seattle, WA (US)

(72) Inventors: Steve Quarre, Woodinville, WA (US); Ronald Seubert, Sammamish, WA (US)

(73) Assignee: RARECYTE, INC., Seattle, WA (US)

( * ) Notice: Subject to any disclaimer, the term of this patent is extended or adjusted under 35 U.S.C. 154(b) by 0 days.

(21) Appl. No.: 14/643,891

(22) Filed: Mar. 10, 2015

(65) Prior Publication Data
US 2015/0182962 A1 Jul. 2, 2015

Related U.S. Application Data

(63) Continuation-in-part of application No. 14/248,510, filed on Apr. 9, 2014.

(60) Provisional application No. 61/810,834, filed on Apr. 11, 2013, provisional application No. 61/922,931, filed on Jan. 2, 2014.

(51) Int. Cl.
*B01L 3/02* (2006.01)
*G01N 35/10* (2006.01)
*G01N 15/10* (2006.01)

(52) U.S. Cl.
CPC .............. *B01L 3/0275* (2013.01); *B01L 3/0217* (2013.01); *G01N 35/1009* (2013.01); *B01L 2200/0657* (2013.01); *B01L 2200/0668* (2013.01); *G01N 2015/1006* (2013.01); *G01N 2015/1081* (2013.01)

(58) Field of Classification Search
CPC ........................... G01N 35/10; G01N 35/1002
USPC .................................. 422/508, 511, 515, 509
See application file for complete search history.

(56) References Cited

U.S. PATENT DOCUMENTS

| | | | |
|---|---|---|---|
| 3,542,277 A | 11/1970 | Andrews | |
| 4,917,274 A | 4/1990 | Asa et al. | |
| 5,468,453 A * | 11/1995 | Holt | B01L 3/0275 422/509 |
| 6,354,479 B1 | 3/2002 | Reiber et al. | |
| 6,702,990 B1 * | 3/2004 | Camacho | B01L 3/0217 204/613 |
| 8,043,865 B2 * | 10/2011 | Karg | B01F 3/0865 422/501 |
| 8,871,157 B2 * | 10/2014 | Homberg | B01L 3/0237 422/515 |
| 2002/0134175 A1 * | 9/2002 | Mehra | B01L 3/0275 73/863.85 |
| 2003/0165408 A1 * | 9/2003 | Takeda | B01L 3/0275 422/525 |
| 2005/0016921 A1 * | 1/2005 | Gjerde | G01N 35/10 210/638 |
| 2009/0202392 A1 * | 8/2009 | Urano | B01L 3/0275 422/400 |
| 2010/0323372 A1 * | 12/2010 | Fulton | B01J 20/28004 435/7.72 |
| 2011/0038769 A1 * | 2/2011 | Gjerde | B01J 20/285 422/524 |
| 2011/0300035 A1 * | 12/2011 | Taniguchi | G01N 35/1004 422/509 |
| 2012/0121482 A1 * | 5/2012 | Ochman | B29C 67/0014 422/524 |
| 2012/0291872 A1 * | 11/2012 | Brady | G01N 35/1065 137/3 |

FOREIGN PATENT DOCUMENTS

WO  WO2010098549 A2  9/2010

\* cited by examiner

*Primary Examiner* — Jill Warden
*Assistant Examiner* — Brittany Fisher

(57) ABSTRACT

This disclosure is directed to a device and a system for aspirating and dispensing a target analyte, target material, or fluid. A picker may aspirate and dispense the desired material by introducing a pressure gradient. The picker may include a hydraulic fluid to hydraulically couple at least two components, such as a moveable pump component and a cannula.

18 Claims, 20 Drawing Sheets

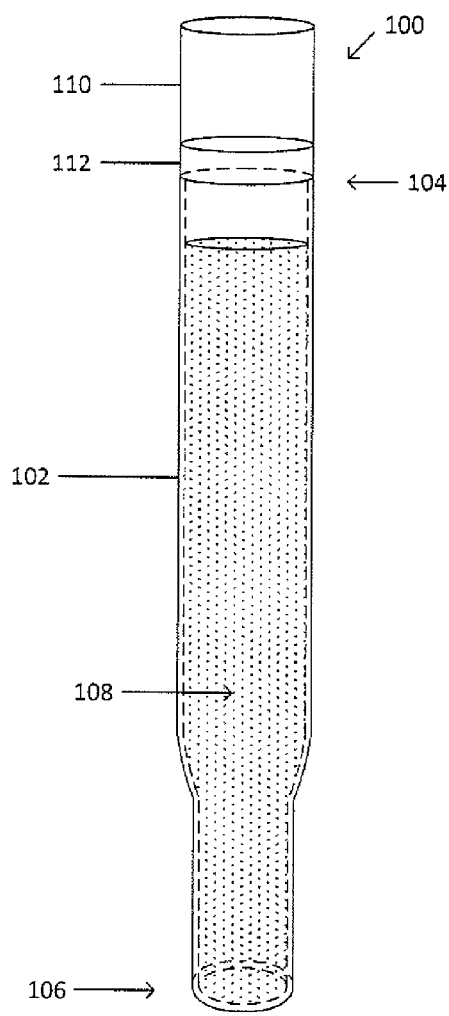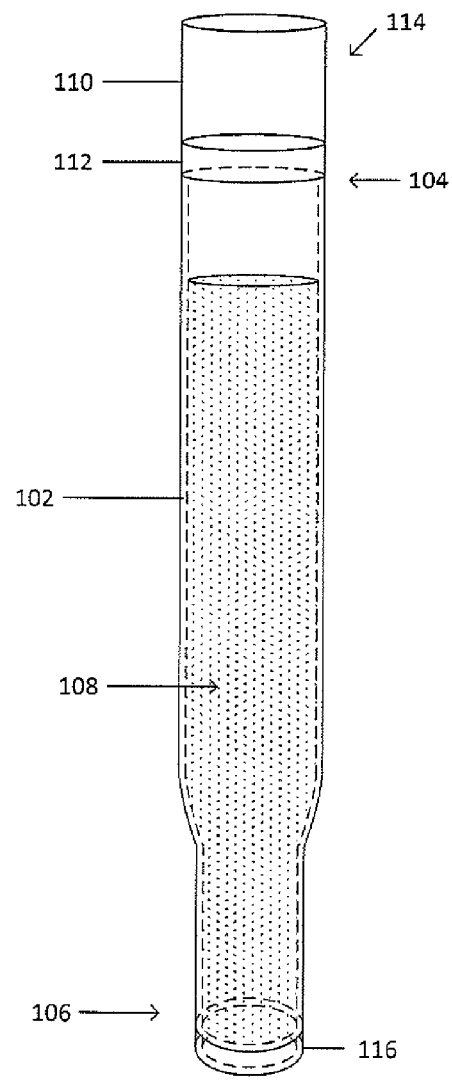
Fig. 1A
Fig. 1B

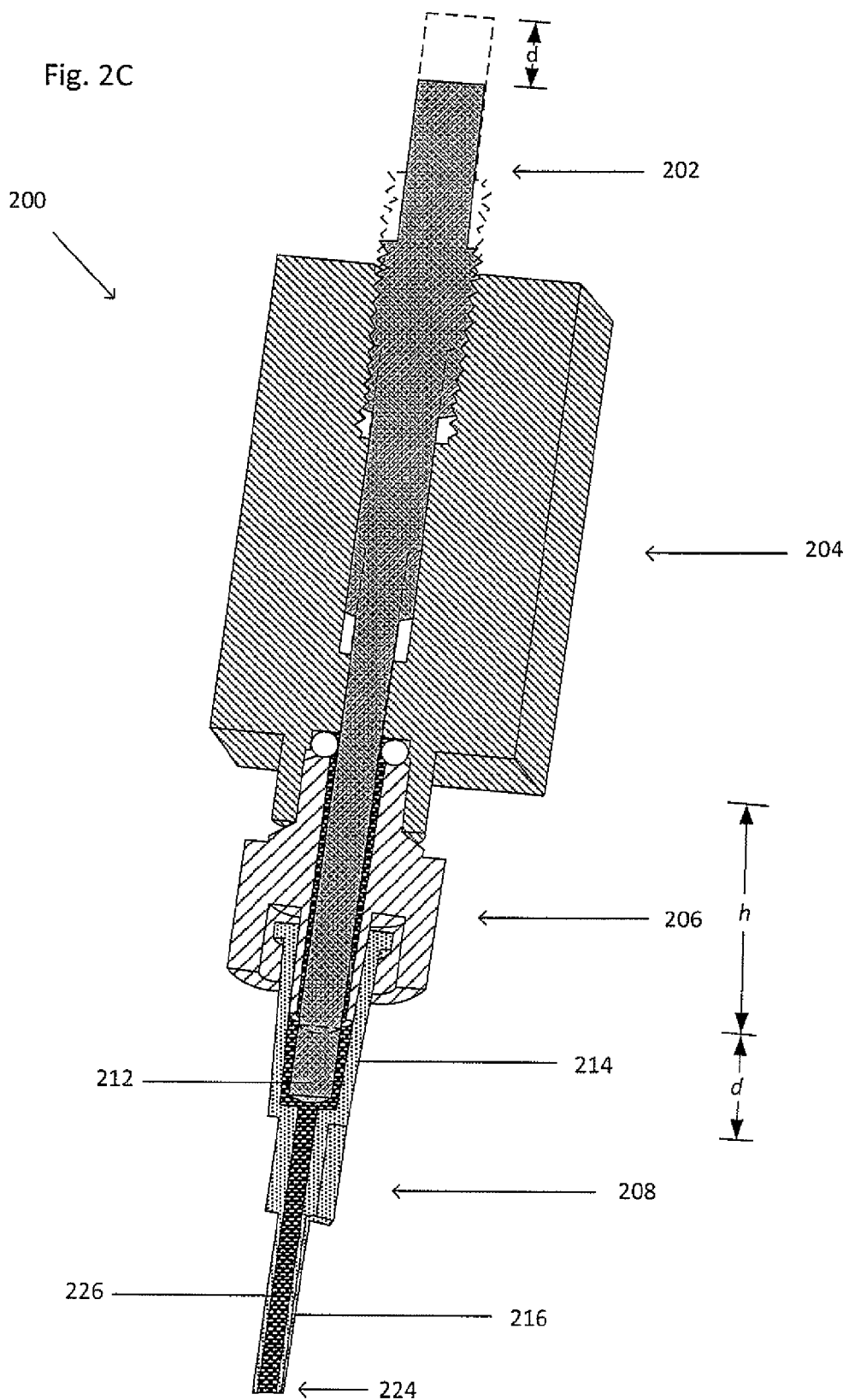

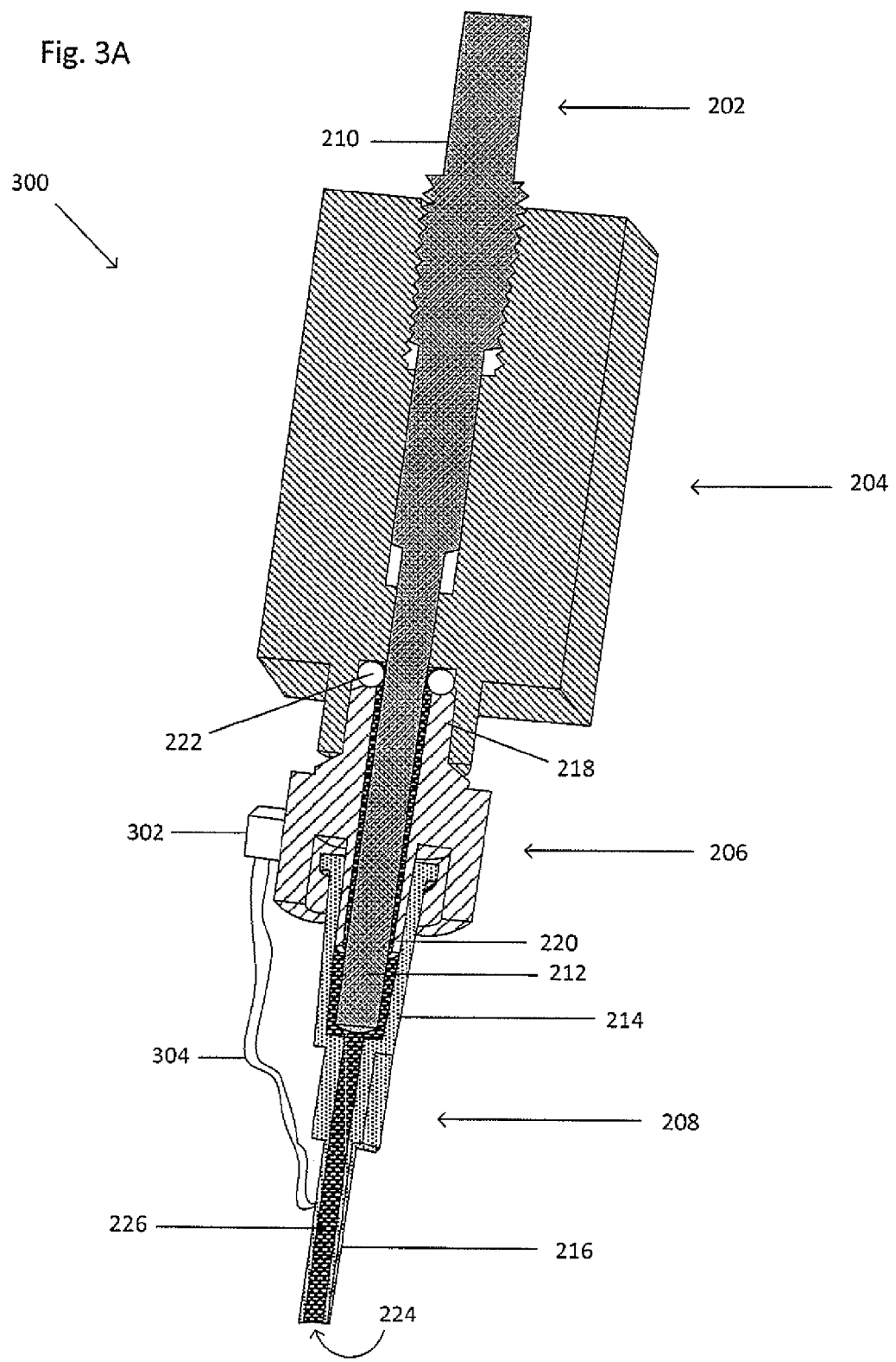

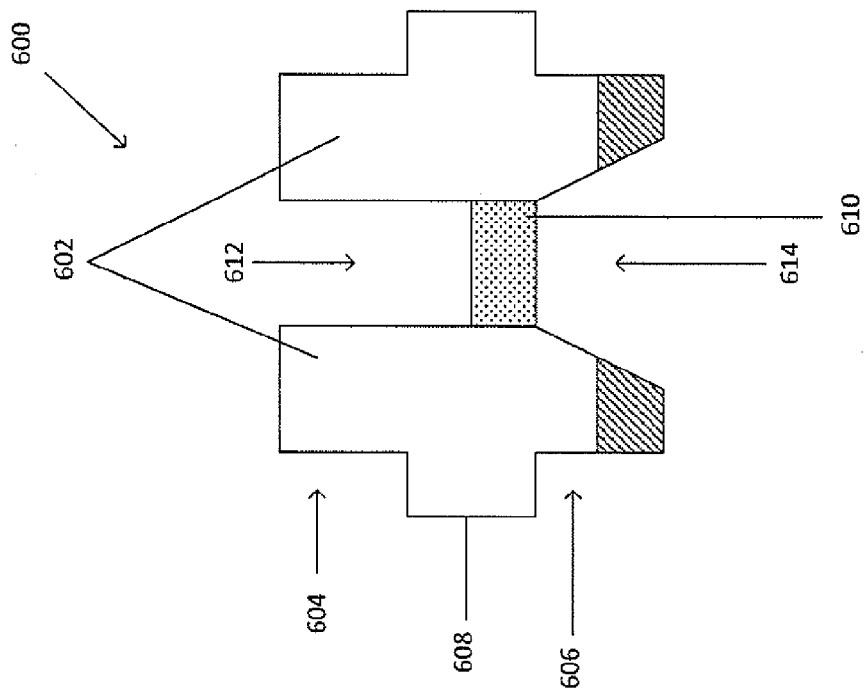
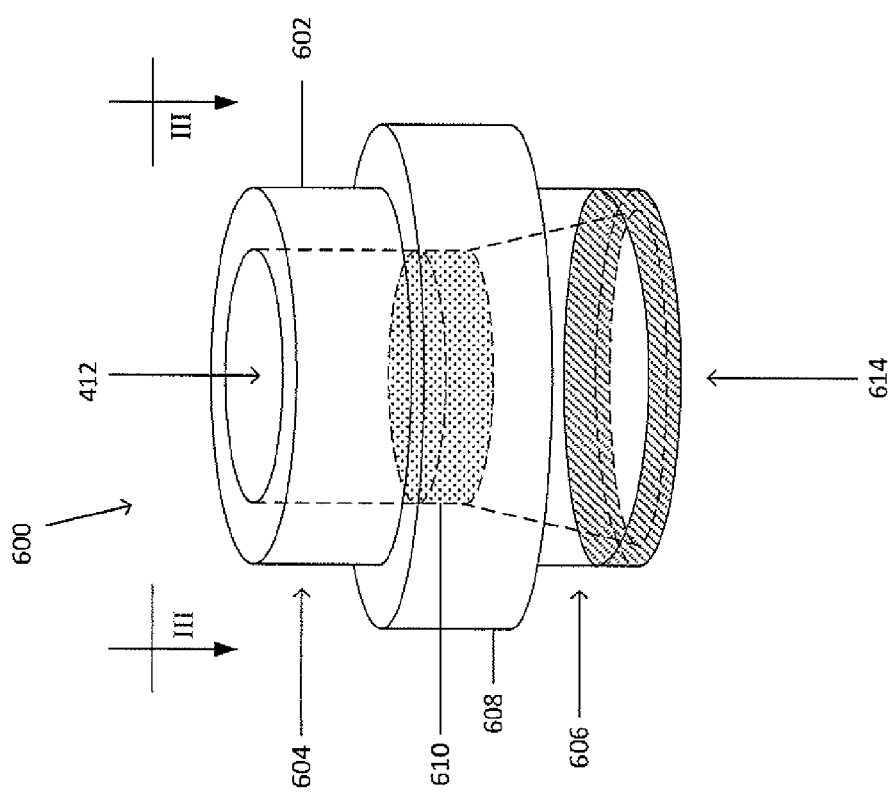

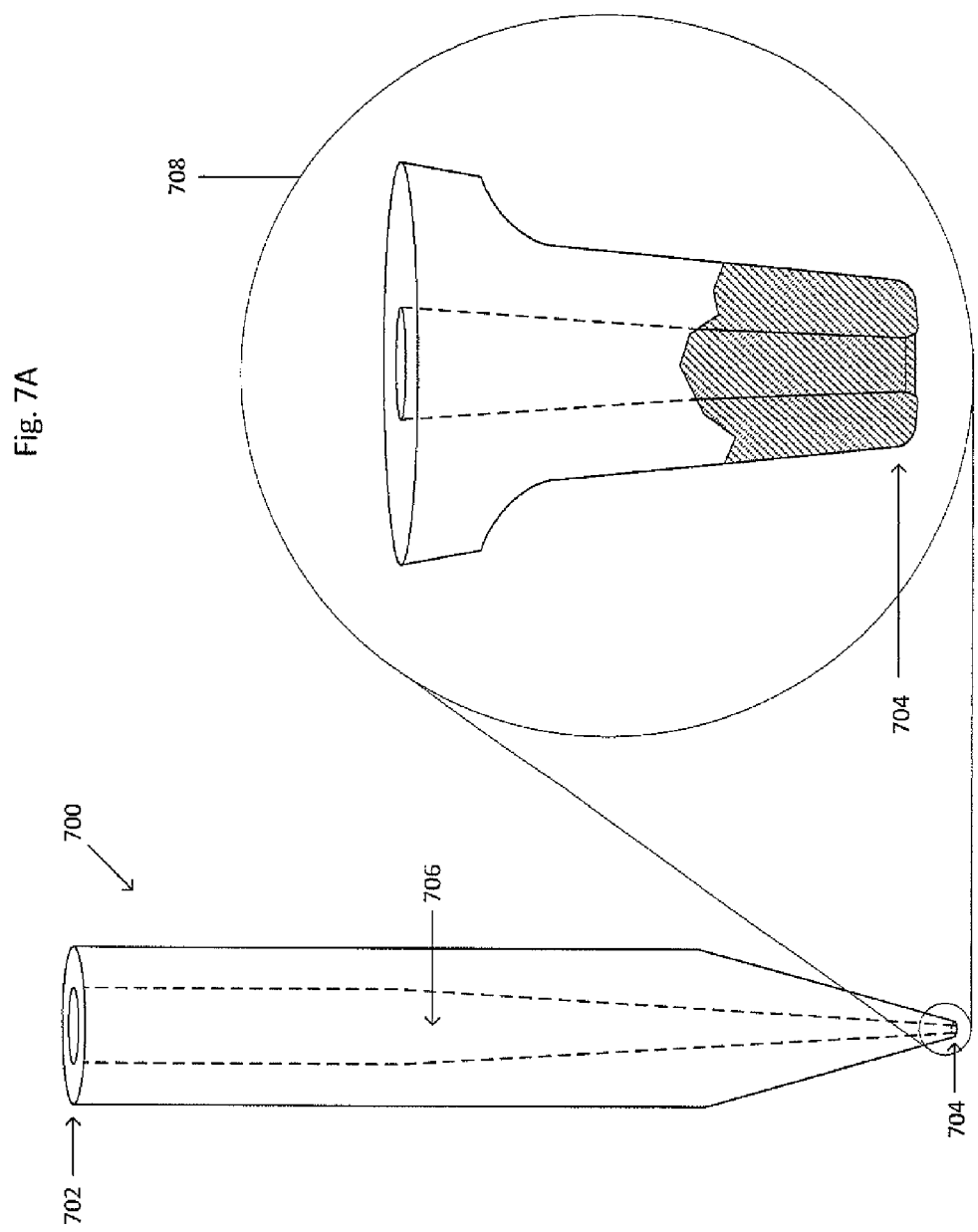

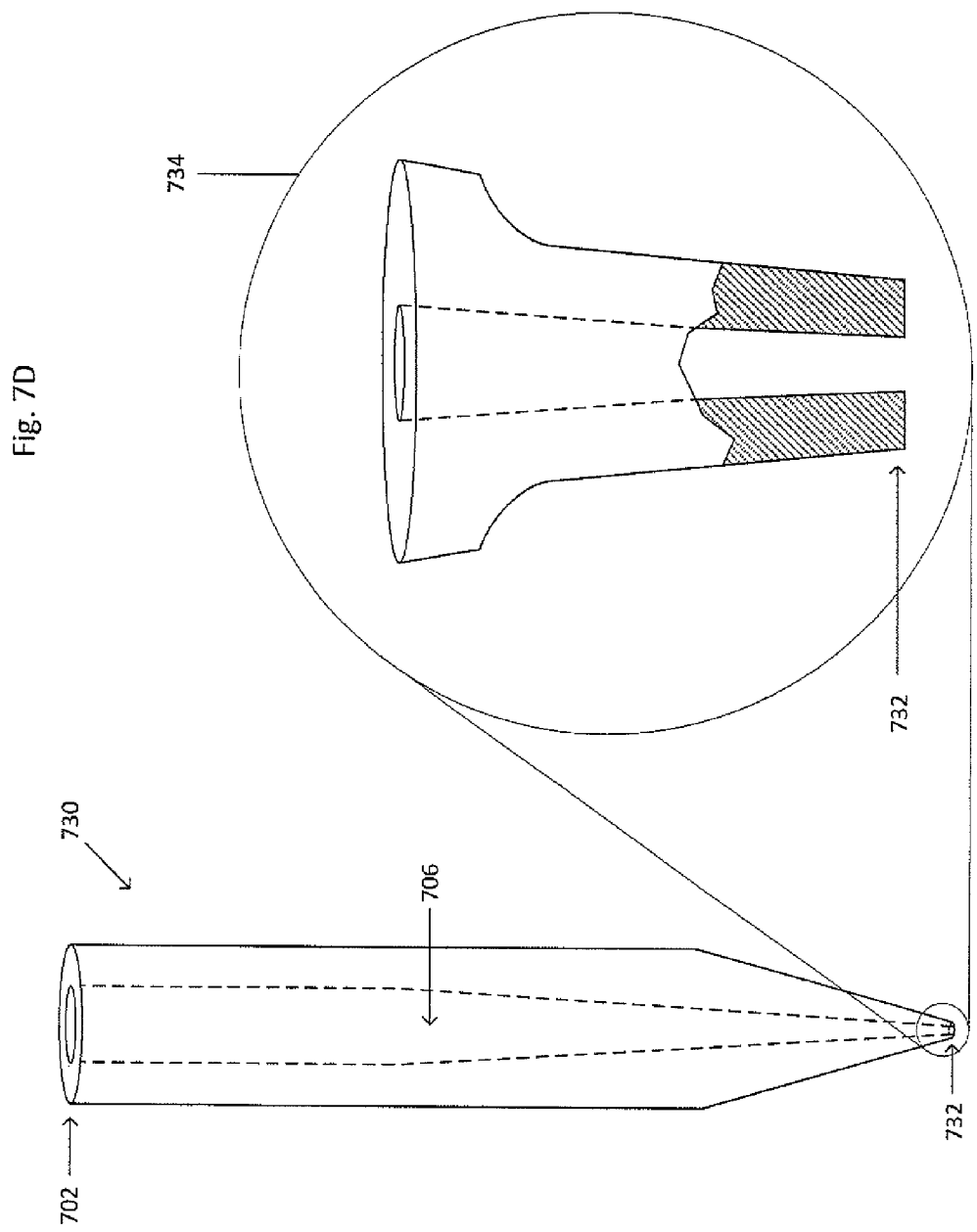

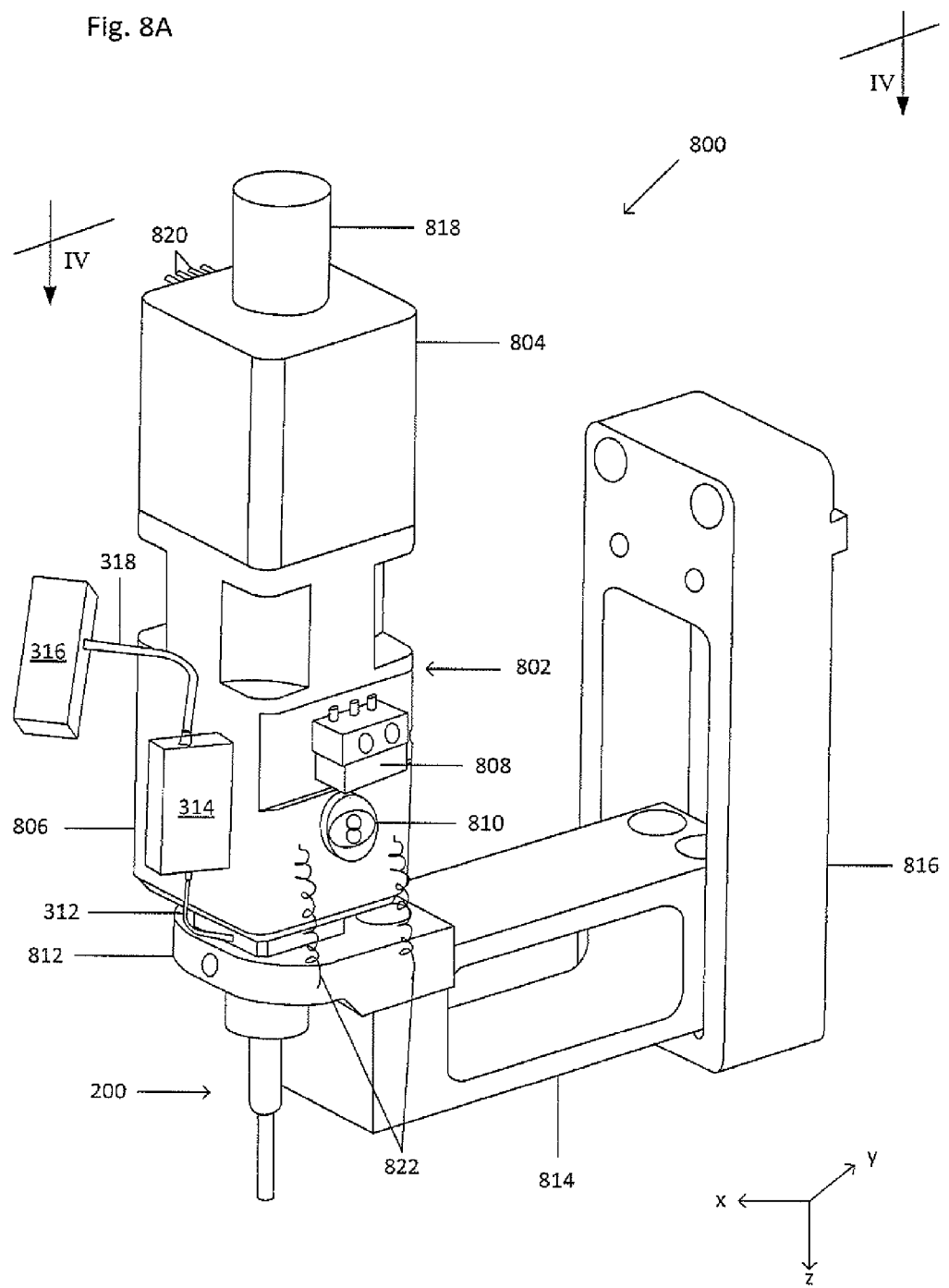

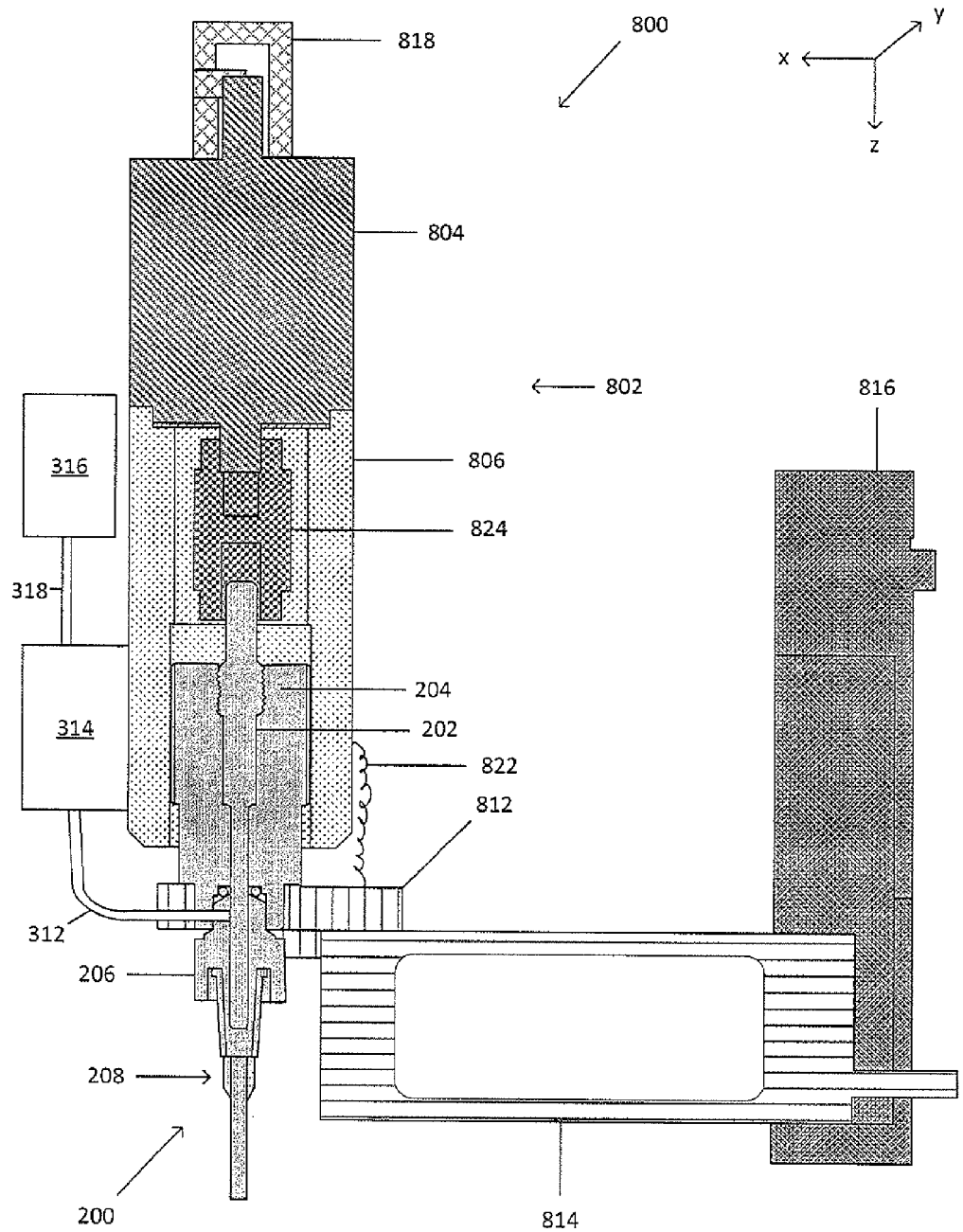

DEVICE, SYSTEM, AND METHOD FOR SELECTING A TARGET ANALYTE OR FLUID

CROSS-REFERENCE TO A RELATED APPLICATION

This application is a continuation-in-part of application Ser. No. 14/248,510, filed Apr. 9, 2014, which claims the benefit of Provisional Application No. 61/810,834, filed Apr. 11, 2013, and Provisional Application No. 61/922,931, filed Jan. 2, 2014.

TECHNICAL FIELD

This disclosure relates generally to micromanipulation of a target analyte, though more specifically, to picking and isolating the target analyte.

BACKGROUND

Suspensions often include materials of interest that are difficult to detect, extract and isolate for analysis. For instance, whole blood is a suspension of materials in a fluid. The materials include billions of red and white blood cells and platelets in a proteinaceous fluid called plasma. Whole blood is routinely examined for the presence of abnormal organisms or cells, such as fetal cells, endothelial cells, epithelial cells, parasites, bacteria, and inflammatory cells, and viruses, including HIV, cytomegalovirus, hepatitis C virus, and Epstein-Barr virus, and nucleic acids. Currently, practitioners, researchers, and those working with blood samples try to separate, isolate, and extract certain components of a peripheral blood sample for examination. Typical techniques used to analyze a blood sample include the steps of smearing a film of blood on a slide and staining the film in a way that enables certain components to be examined by bright field microscopy.

On the other hand, materials of interest composed of particles that occur in very low numbers are especially difficult if not impossible to detect and analyze using many existing techniques. Consider, for instance, circulating tumor cells ("CTCs"), which are cancer cells that have detached from a tumor, circulate in the bloodstream, and may be regarded as seeds for subsequent growth of additional tumors (i.e., metastasis) in different tissues. The ability to accurately detect and analyze CTCs is of particular interest to oncologists and cancer researchers, but CTCs occur in very low numbers in peripheral whole blood samples. For instance, a 7.5 ml sample of peripheral whole blood that contains as few as 3 CTCs is considered clinically relevant in the diagnosis and treatment of a cancer patient. However, detecting even 1 CTC in a 7.5 ml blood sample may be clinically relevant and is equivalent to detecting 1 CTC in a background of about 50 billion red and white blood cells. Using existing techniques to find, isolate and extract as few as 3 CTCs of a whole blood sample is extremely time consuming, costly and is extremely difficult to accomplish.

As a result, practitioners, researchers, and those working with suspensions continue to seek systems and methods to more efficiently and accurately detect, isolate and extract target materials of a suspension.

DESCRIPTION OF THE DRAWINGS

FIGS. 1A-1D show examples of a picker.
FIG. 2A-2D show an example picker.
FIG. 3A shows an example picker.
FIGS. 6A-6B show an example fluorescent picker tip.
FIGS. 7A-7E show example picker tips.
FIGS. 8A-8B show an example picking system.

DETAILED DESCRIPTION

Figure 1C:
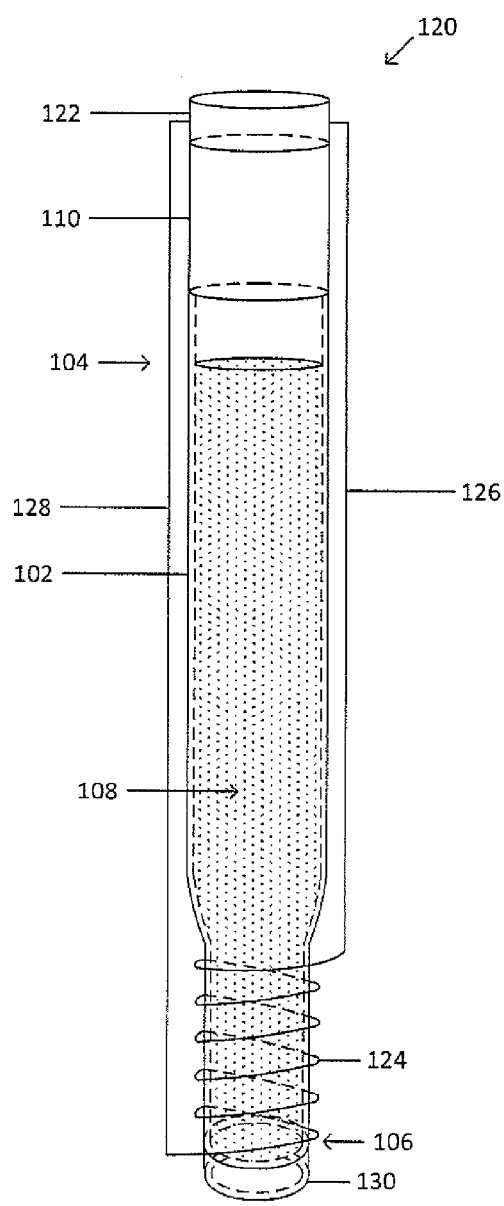

This disclosure is directed to a device and a system for aspirating and dispensing a target analyte, target material, or fluid. A picker may aspirate and dispense the desired material by introducing a pressure gradient. The picker may include a hydraulic fluid to hydraulically couple at least two components, such as a moveable pump component and a cannula.

Picker and Picking System

FIG. 1A shows an example picker 100. The picker 100 includes a main body 102, a back end 104, and a tip 106. The picker 100 may be solid or may be a hollow tube having an inner chamber for holding a liquid, target analyte, or any other appropriate material. When the picker 100 is a hollow tube, the picker 100 may also include a liquid 108 within the inner chamber of the picker 100, where the liquid may be a solution, a buffer, a ferrofluid, or the like. The picker 100 may be used to manipulate a target analyte. The target analyte may be manipulated, such as by moving, removal, or isolation, when the specific target analyte is in a vessel, such as a tube or a well, or on a slide. The target analyte can be isolated through the introduction of a force, thereby attracting or pulling the target analyte. The tip 106 engages the target analyte for moving, removal, or isolation. The force may be created with suction or a pressure gradient, such as a vacuum. The back end 104 may be connected to a pump 110, such as a vacuum pump, a lead screw, or a hand pump with a wheel, to aid in providing the force for moving, removal, or isolation. The picker 100 may also include a light source 112, such as an LED, to illuminate an area in which the target analyte may be present. The light source 112 may be located anywhere along the main body 102, including the back end 104 and the tip 106. When the light source 112 is located at the back end 104, the main body 102 may be composed of a material capable of propagating or transmitting a light signal produced by the light source 112, such that the light signal exits at the tip 106 to illuminate the desired area. The light source 112 may be connected to a power supply (not shown), such as a battery, to supply current or power.

FIG. 1B shows an example picker 114. The picker 114 is similar to the picker 100, except that picker 114 includes a permanent magnet 116, such as a donut-shaped magnet. The permanent magnet 116 generates a magnetic field for attracting a particle of a target analyte-particle complex, a target analyte having been previously conjugated with the particle to form the target analyte-particle complex. The picker 114 may also include a magnetizable material to extend or transmit the magnetic field produced by the magnet. The permanent magnet 116 may be located at the tip 106 or at or near the back end 104. The permanent magnet 116 may be removable. Alternatively, the fluid, such as a ferrofluid, within the picker 114 may be used to generate the magnetic field or magnetic gradient.

FIG. 1C shows an example picker 120. The picker 120 is similar to the picker 100, except that picker 120 includes an electromagnet. The electromagnet includes a power source 122, a first lead 126, a second lead 128, and a coil 124. The power source 122 may be, but is not limited to, a battery, a DC supply, or an AC supply. The electromagnet generates a magnetic field for attracting a particle of a target analyte-particle complex, a target analyte having been previously conjugated with the particle to form the target analyte-particle complex. The picker 120 may be composed of a magnetizable material to extend or transmit the magnetic field produced by the magnet. The first lead 126, the second 128, and the coil 124 may be located outside of a wall of the picker 120, may be embedded with the wall of the picker 120, or may be located inside of the picker 120. The picker 120 may also include a light source 130, such as an LED, to illuminate an area in which the target analyte may be present. The light source 130 may be located anywhere along the main body 102, including the back end 104 and the tip 106. When the light source 130 is located at the back end 104, the main body 102 may be composed of a material capable of propagating or transmitting a light signal produced by the light source 130, such that the light signal exits at the tip 106 to illuminate the desired area. The light source 130 may be connected to a power supply (not shown), such as a battery, to supply current or power.

Figure 1D:
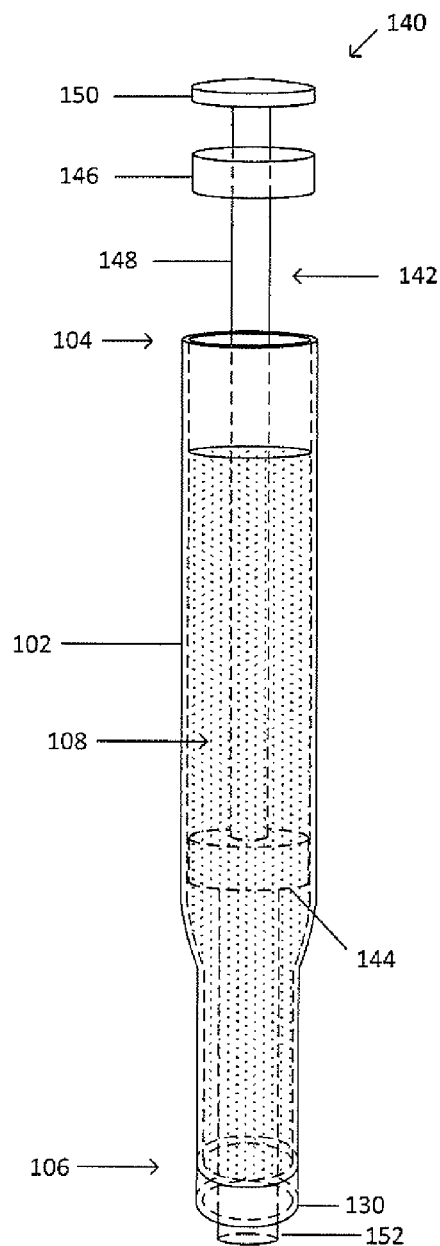

FIG. 1D shows an example picker 140. The picker 140 includes a retractable shaft 142, the retractable shaft 142 being thinner than the main body 102 and being extendable from the tip 106. The retractable shaft 142 can be located within the main body 102, can be extended out of the tip 106 to engage a target analyte, and can be retracted into the main body 102. When the target analyte attaches to the retractable shaft 142, the target analyte can be drawn into the main body 102. The retractable shaft 142 may include an engagement portion 152, a stopper 144, a grip 150, and a rod 148. The engagement portion 152 may be extended out of the tip 106 to engage the target analyte. The stopper 144 may be sized to fit within the main body 102, but be larger than the tip 106 or a taper from the main body 102 to the tip 106, thereby preventing the retractable shaft 142 from extending too far from the tip 106. The grip 150 may allow for engagement of the retractable shaft 142, so as to properly move the retractable shaft 142. The rod 148 may connect the stopper 144 or the engagement portion 146 to the grip 140. The retractable shaft 142 may also be made magnetizable by including a magnet 146 disposed on or within the retractable shaft 142. The magnetic field or magnetic gradient may be removed or deactivated, such as by removing the magnet 146 or turning off an electromagnet. The target analyte-particle complex is no longer attracted and held to the retractable shaft 142 causing the target analyte-particle complex to remain within the liquid in the main body 102. The picker 140 may also include a light source 130, such as an LED, to illuminate an area in which the target analyte may be present. The light source 130 may be located anywhere along the main body 102, including the back end 104 and the tip 106. When the light source 130 is located at the back end 104, the main body 102 may be composed of a material capable of propagating or transmitting a light signal produced by the light source 130, such that the light signal exits at the tip 106 to illuminate the desired area. The light source 130 may be connected to a power supply (not shown), such as a battery, to supply current or power.

Alternatively, the retractable shaft 142 may be magnetized by an electromagnet, such as a coil wrapped around a segment of or the entire retractable shaft 142. Alternatively, the picker 140 may include a pump (not shown), such as a vacuum pump, a lead screw, or a hand pump with a wheel, to aid in providing the force for moving, removal, or isolation.

Figure 2A:
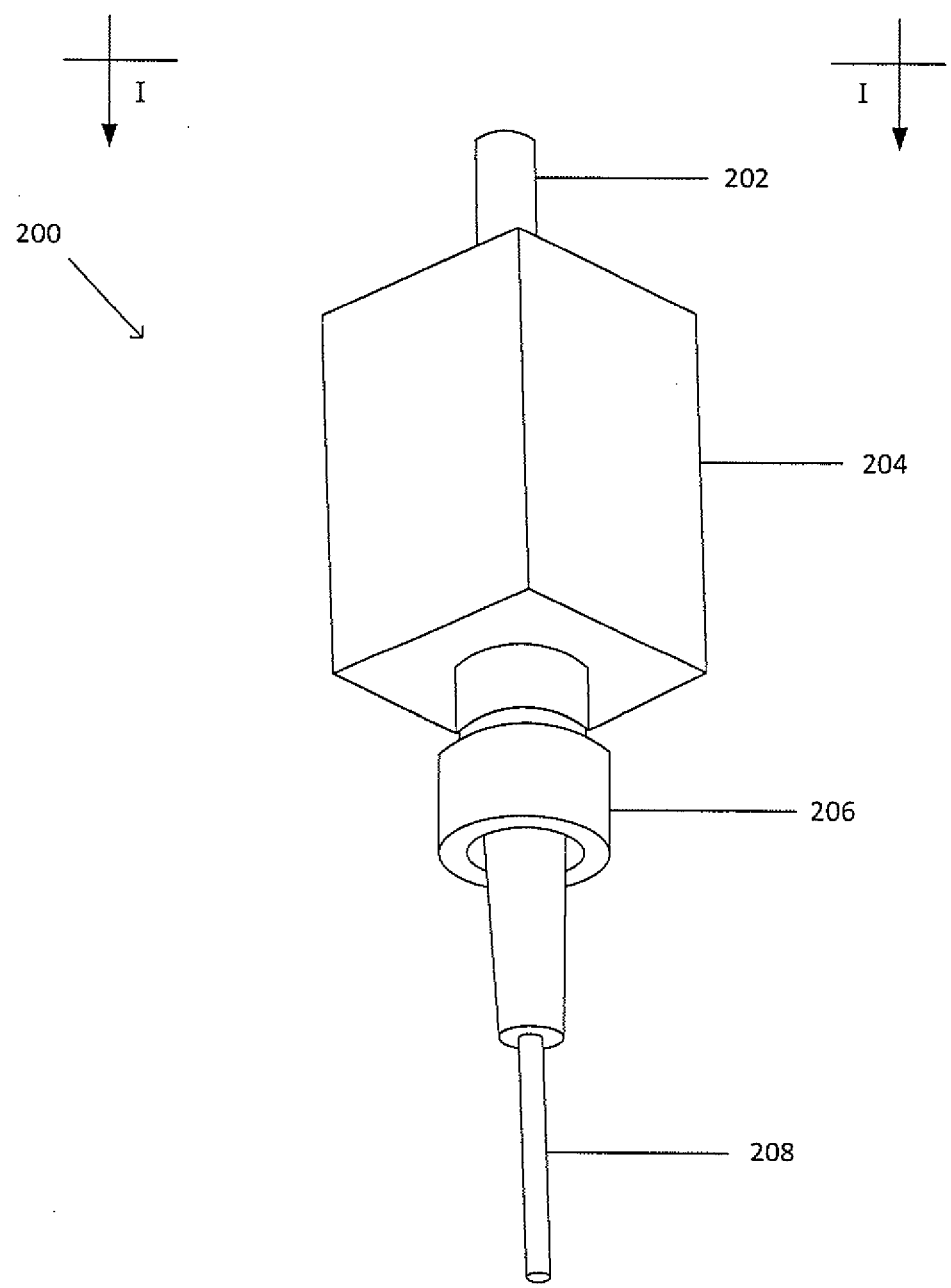
Figure 2B:
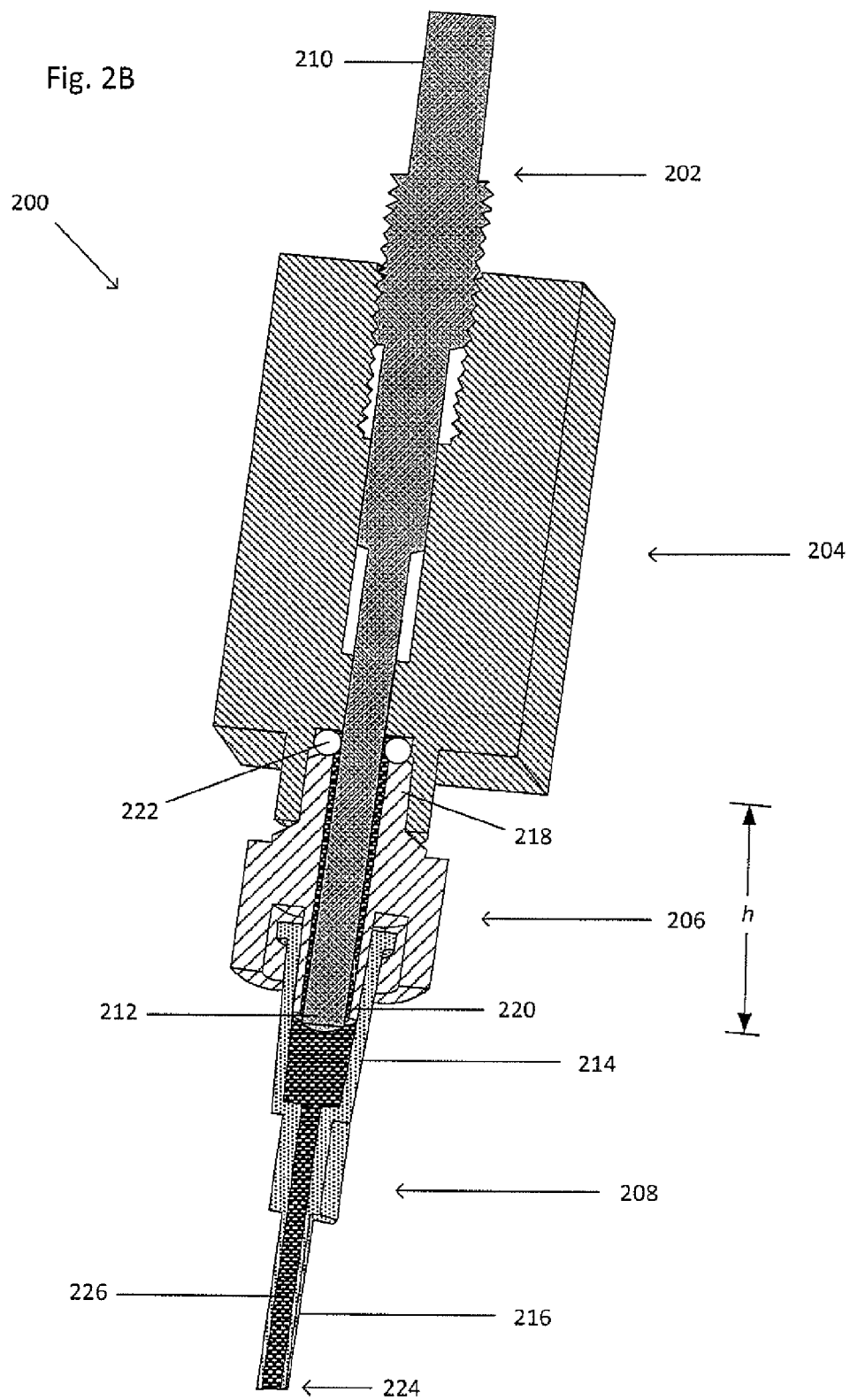

FIG. 2A shows an example picker 200. FIG. 2B shows a cross-sectional view of the example picker 200 taken along the line I-I. The picker 200 includes a piston 202, a pump block 204, and a cannula 208. The picker 200 may also include a fitting 206 with a first side 218 and a second side 220. The piston 202 includes a first end 210 and a second end 212. The cannula 208 includes an adapter 214 and a tube end 216, the tube end 216 including a picker tip 224. The first side 218 of the fitting 206 mates with the pump block 204, such as by a press-fit, detents, notches, complementary threads, or the like. A seal 222 may be formed between the first side 218 of the fitting 206 or the adapter 214 of the cannula 208 and the pump block 204, such as by an O-ring, grease, silicone grease, or the like, to close the picker 200. The adapter 214 of the cannula 208 may mate with the second side 220 of the fitting 206 or the pump block 204, such as by a press-fit, detents, notches, complementary threads, or the like. In other words, the cannula 208, without the inclusion of the fitting 206, may be connected directly to the pump block 204.

The piston 202 may be any appropriate length. The second end 212 of the piston 202 may be located within the pump block 204, within the fitting 206, within the adapter 214 of the cannula 208, or within the tube end 216 of the cannula 208. The second end 212 of the piston 210 may extend through the seal 222. The first end 210 of the piston 202 may be located within the pump block 204 or may extend out of a side of the pump block 204 opposite the side of the pump block 204 that is connected, whether directly or indirectly, to the cannula 208. The piston 202 and the cannula 208 may substantially share a central axis. The positioning of the piston 202 relative to the cannula 208 reduces or eliminates dead volume.

The pump block 204 at least partially houses the piston 202 and allows for translation of the piston 202 relative to the pump block 204. Moving the piston 202, such as a lead screw or rod, upwards within the pump block 204 may create a negative pressure at the tube end 216 so as to draw a target analyte or fluid from the suspension into the cannula 208 or may create a positive pressure to expel a target analyte or fluid located within the cannula 208 from the tube end 216. The piston 202 may be connected to a motor or an actuator to drive the piston 202 up and down, thereby creating the desired pressure differential. The pump block 204 may include a complementary mating feature, such as threads or a bore, to accept and mate with the piston 202. When the piston 202 and the pump block 204 include complementary threads, the piston 202 may be rotated to cause the desired translation. A full rotation of the piston 202 may include any number of steps, including 1-10,000 steps. Those steps may then include any number of micro-steps, including 1-10,000 micro-steps. Each step or micro-step may draw in a volume approximately equal to or less than 1 picoliter, 10 picoliters, 100 picoliters, 1 nanoliter, 1 microliter, or 1 milliliter. A piezo-electric pump (not shown) may also be placed in series with the piston 202, such as on the second 212 of the piston 202, thereby allowing for even smaller volumes to be processed. The piezo-electric pump (not shown) may be connected to a voltage source (not shown) to cause the deformation required to generate the desired negative or positive pressure.

The piston 202 and the cannula 208 may be hydraulically coupled, such that the volume from the tube end 216 of the cannula 208 to the seal 222 is filled with a hydraulic fluid 226. The volume from the tube end 216 of the cannula 208 to the seal 222 filled with the hydraulic fluid 226, which may also be referred to as a pump volume, may be contained in a rigid structure, rather than a flexible structure, to maintain the hydraulic coupling efficiency. The hydraulic fluid 226 may be incompressible or have low compressibility. The hydraulic fluid 226 may be a solution, an oil, a liquid metal, a buffer, water, or the like. Hydraulically coupling the piston 202 and the cannula 208 provides better small volume control (i.e. full piston travel draws/expels 1-50 µL) than a non-hydraulically coupled picker (i.e. filled with air). The hydraulic fluid 226 may include a fluid plug, such that two volumes of the hydraulic fluid 226 are separated by a volume of air or a different liquid. The pump volume, which is constant, satisfies the condition given by:

$$V_P = V_{HF} + V_{MPC} + V_{PM} + V_{Air},$$

where $V_P$ represents the pump volume, $V_{HF}$ represents the volume of the hydraulic fluid, $V_{MPC}$ represents the volume of the portion of the at least one movable pump component within the pump volume, where $V_{PM}$ represents the volume of any picked or aspirated material, and where $V_{Air}$ represents the volume of air within the pump volume. In this instance, the at least one moveable pump component is the piston 202. Because the pump volume is constant and the piston 202 may be substantially cylindrical, the volume of the piston 202 satisfies the conditions given by:

$$V_{MPC} = \pi r^2 h,$$

where $V_{MPC}$ represents the at least one moveable pump component (i.e. the piston 202), r represents the radius of the second end 212 of the piston 202, h represents the amount of the piston 202 within the pump volume. Alternatively, the piston 202 may be substantially square, rectangular, triangular, pentagonal, or any other appropriate polygonal shape. Accordingly, the volume of the piston 202 would satisfy the equations for the volumes of the respective shapes.

FIG. 2C shows the picker 200 with the piston 202 having been driven towards the picker tip 224. The distance (d) traveled by the piston 202 may be used to calculate the new volume of the piston 202 within the pump volume based on the shape of the piston 202. The distance (d) may be positive (piston 202 moves towards picker tip 224; and, accordingly, creates a positive pressure gradient) or negative (piston 202 moves away from picker tip 224; and, accordingly, creates a negative pressure gradient). The new volume of the piston 202 therefore satisfies the conditions given by:

$$V_{MPC} = \pi r^2 (h+d),$$

where $V_{MPC}$ represents the at least one moveable pump component (i.e. the piston 202), r represents the radius of the second end 212 of the piston 202, h represents the amount of the piston 202 within the pump volume, and d represents the distance traveled by the piston 202 within the pump volume. With respect to the pump volume equation discussed above ($V_P = V_{HF} + V_{MPC} + V_{PM} + V_{Air}$), the pump volume remains constant because the difference between the first and second volumes occupied by the at least one moveable component (i.e. piston 202) is equal to the amount of the hydraulic fluid 226, picked or aspirated material, and/or air displaced from the pump volume.

Figure 2D:
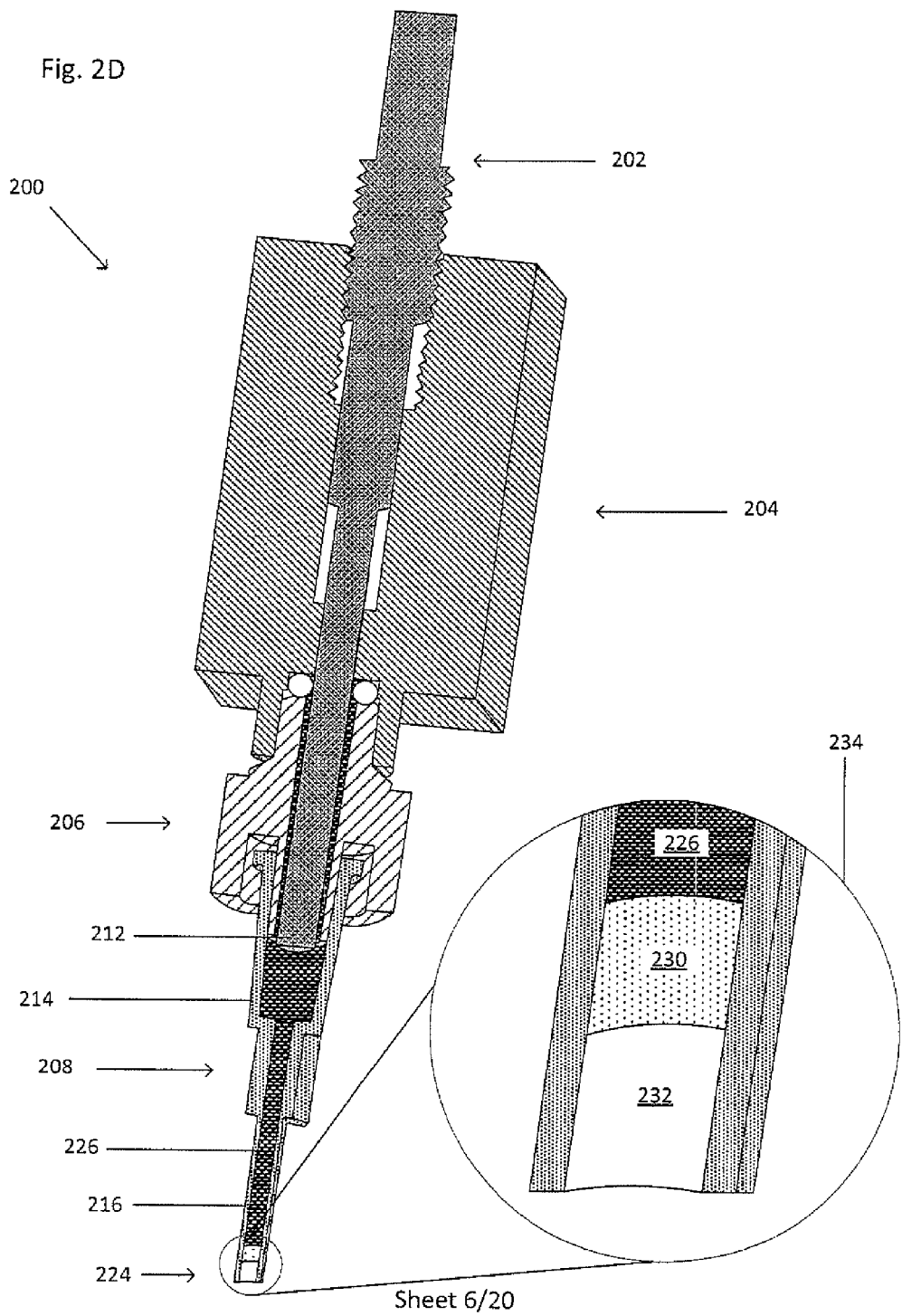

FIG. 2D shows the picker 200 with the piston 202 having been driven away the picker tip 224 and drawing in a target material 230 and air 232. Though FIGS. 2B-2D depict the piston 202 being driven towards and then away from the picker tip 224 to draw in the target material 230, and consequently some air 232, the piston 202 may be driven in any appropriate manner and in appropriate amount to create the desired pressure gradient. It should be further noted that the air 232 may not be drawn in when drawing in the target material 230. The target material 230 may include, but is not limited to, biological matter (i.e. cells, tissue, biological fluid, etc.) or other fluids (i.e. phosphate buffered saline, enzymatic fluids, adherent solutions, water, etc.).

The picker 200 may introduce a magnetic gradient as well, such as by a permanent magnet or an electromagnet, as shown in FIGS. 1B and 1C, respectively, whereby the cannula 208, the hydraulic fluid 226, or the tube end 216 is magnetizable so as to propagate the magnetic gradient. The permanent magnet may be located along the tube end of the cannula, on the piston, or anywhere on the picker tip. When a ferrofluid primes the cannula, the permanent magnet may be located near the adapter. The electromagnet includes a coil, a first lead, a second lead, and a power supply, such as a battery. The coil wraps around the tube end of the cannula or the picker tip. A first end of the first lead is connected to the power supply and a second end of the first lead is connected to a first end of the coil. A first end of the second lead is connected to the power supply and a second end of the second lead is connected to a second end of the coil. The power supply is disposed outside of the pump block.

FIG. 3A shows a picker 300. The picker 300 is similar to the picker 200 except that the picker 300 includes a light source 302. The light source 302 produces a light signal that is propagated or transmitted by the cannula 208 or picker tip inserted into, over, or in-line with the cannula 208. The cannula 208 or the picker tip may be composed of a material capable of propagating or transmitting the light signal produced by the light source 302, such that the light signal exits at the tube end 216 of the cannula 208 or the end of the picker tip furthest away from the pump block 204 to illuminate the desired area and/or stimulate a fluorescent probe bound to a target analyte. When the light source 302, such as an LED, originates at a location other than the tube end 216 of the cannula 208 or the end of the picker tip furthest away from the pump block 204, a cable 304, such as a fiber optic cable, may transmit the light signal to the tube end 216 of the cannula 208 or the end of the picker tip furthest away from the pump block 204 for illumination and/or stimulation purposes. The light source 302 may provide epi-, transmitted, or oblique illumination. The light source 302 may be connected to a power supply (not shown), such as a battery, to supply current or power. Alternatively, the light source 302 may be between the top of the adapter of the cannula 208 and the fitting 206. Alternatively, at least one light source 302 may be embedded in the tube end of the cannula 208. Alternatively, the light source 302 may be located on the adapter 214 or the pump block 204.

Figure 3B:
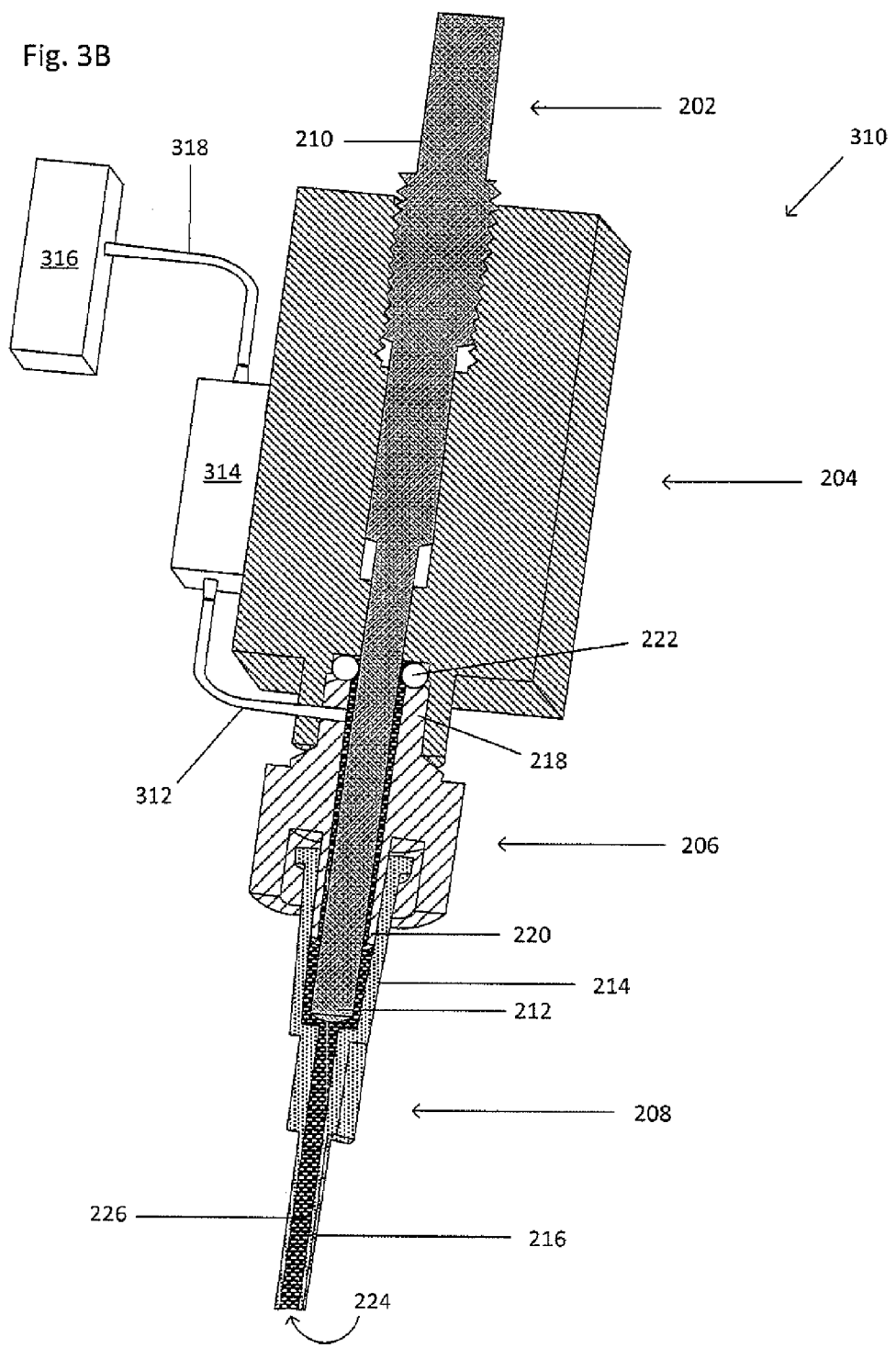
FIG. 3B shows an example picker.

FIG. 3B shows a picker 310. The picker 310 is similar to the picker 200 except that the picker 310 includes a port 312. The port 244 may extend through the second end of the pump block 204 and either the first end 218 of the fitting 206 or the adapter 214 of the cannula 208. The port 312 may be connected to a loader 314, such as a piezoelectric pump, to fill the pump volume. The loader 314 may be connected to a reservoir 316 with a tube 318. The tube 318 may be rigid or flexible. Alternatively, the loader 314 may be interchanged with a pressure sensor (not shown) to measure the pressure within the pump volume to make sure the picker 310 does not clog.

Figure 4A:
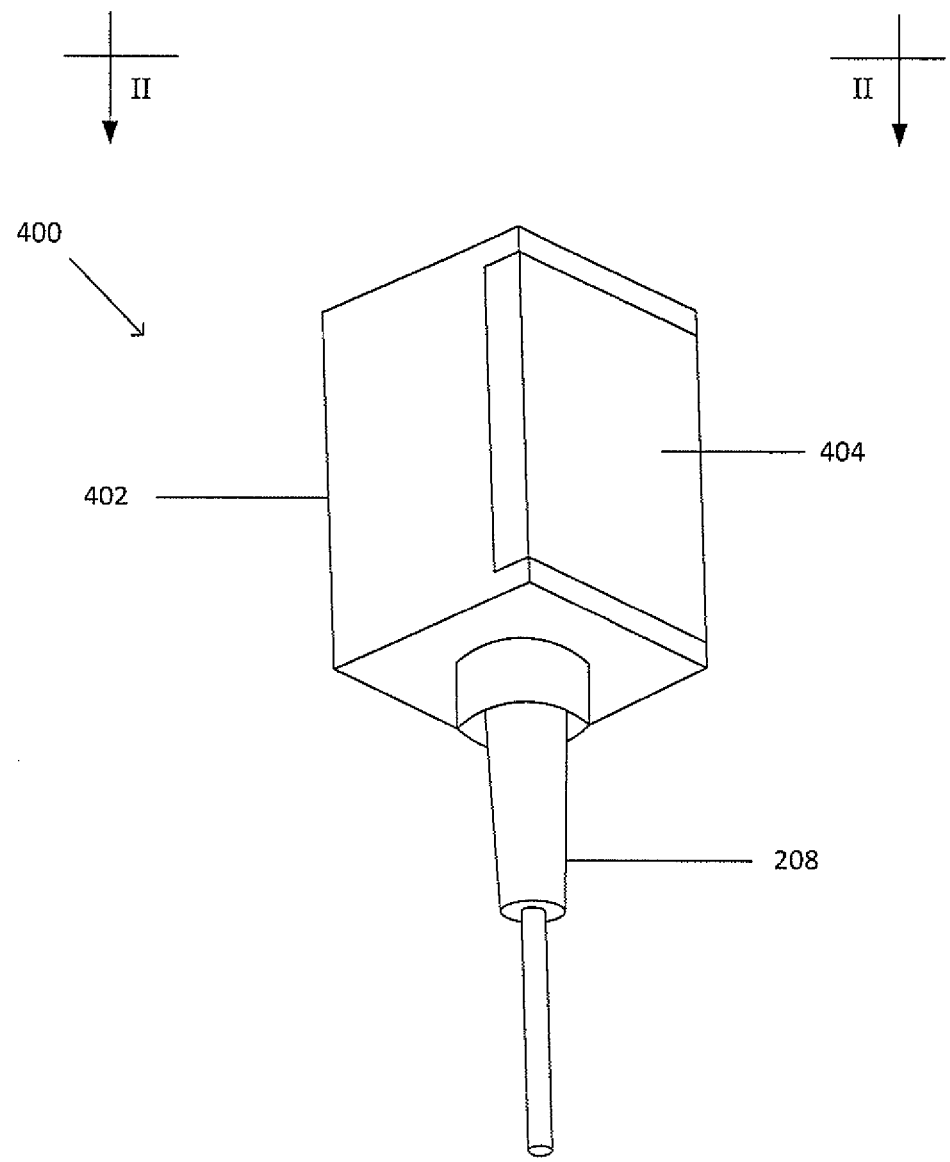
FIGS. 4A-4C show an example picker.
Figure 4B:
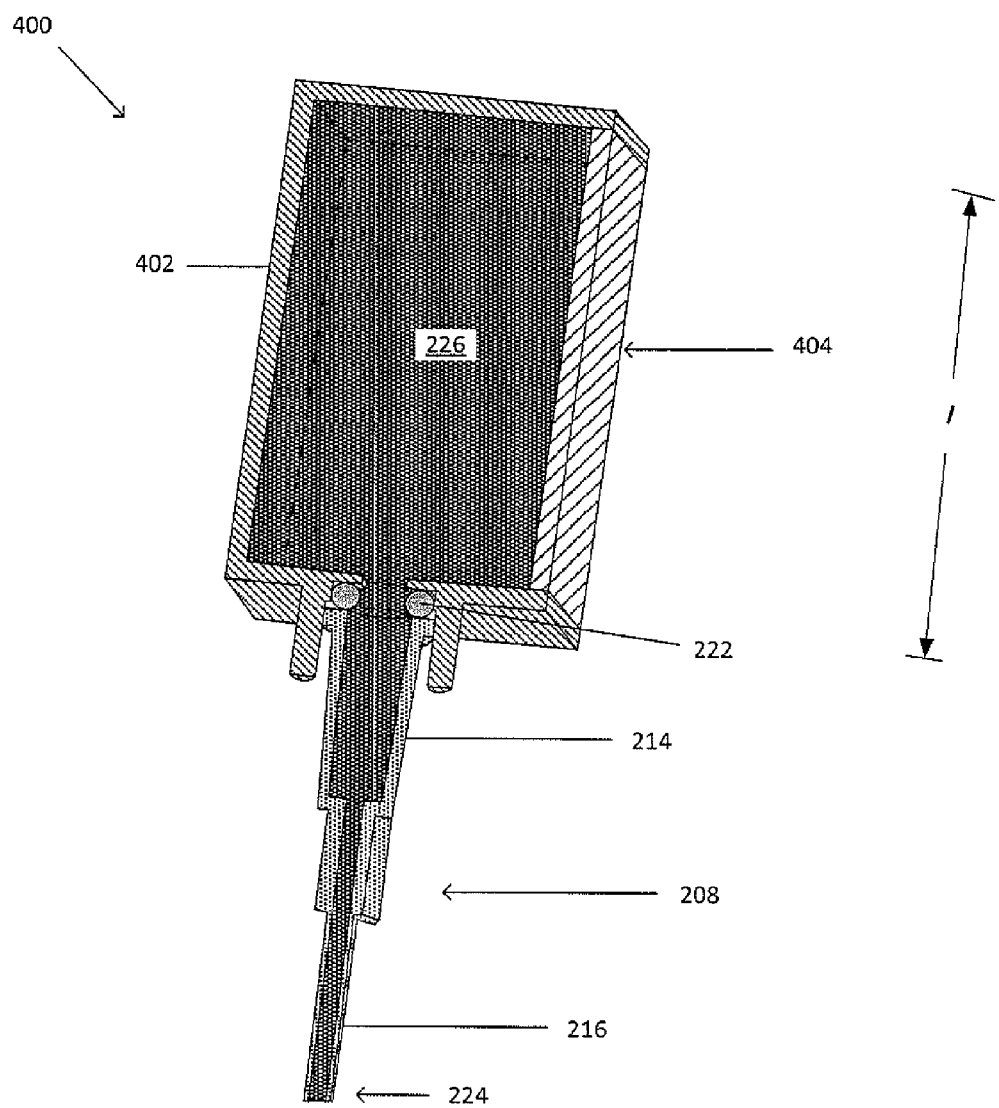
Figure 4C:
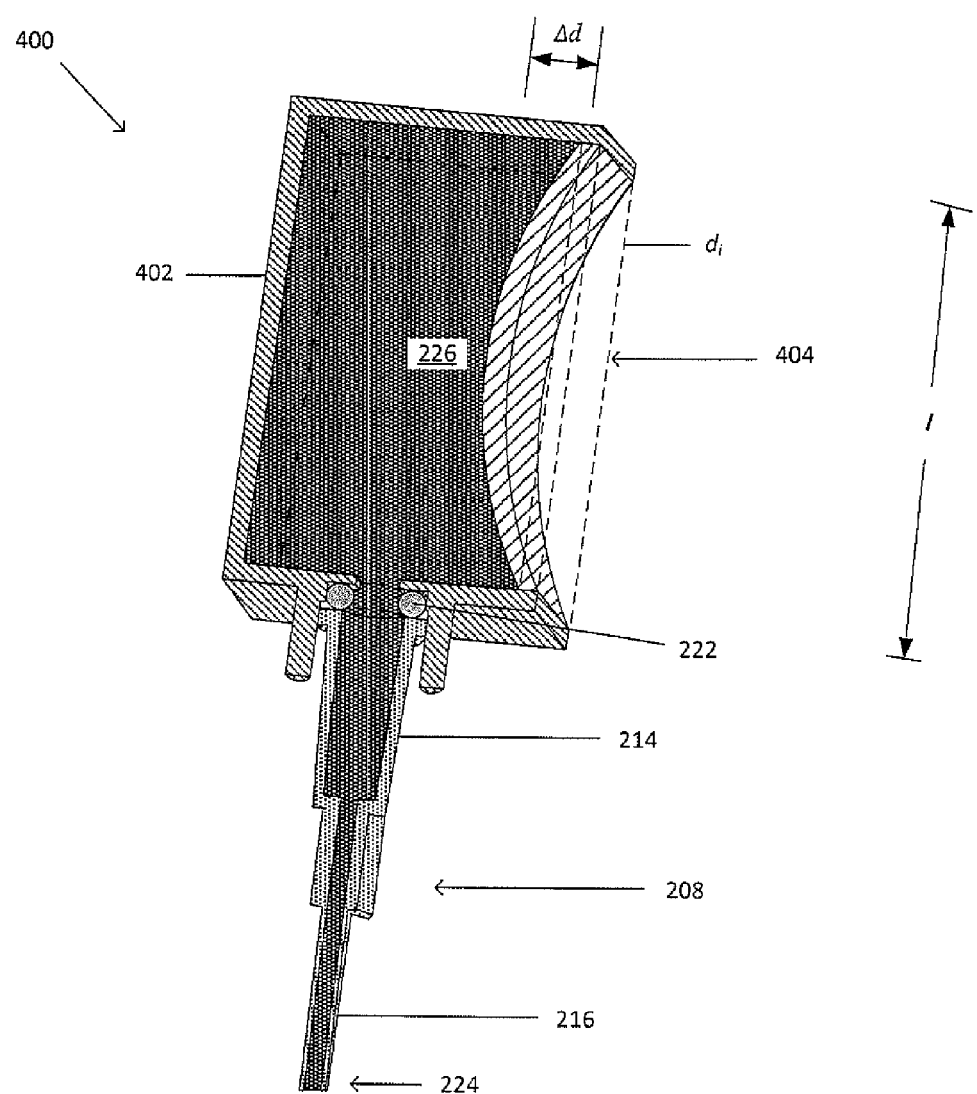

FIG. 4A shows a picker 400. FIGS. 4B and 4C show cross-section views of the picker 400 taken along the line II-II. The picker 400 includes a pump block 402 with a diaphragm 404. The picker 400 also includes the cannula 208, as discussed above, and the seal 222, as discussed above. Further, the seal 222 may be formed between the adapter 214 of the cannula 208 or the fitting (not shown) and the pump block 402, such as by an O-ring or silicone grease, to close the picker 400. The adapter 214 of the cannula 208 may mate with the fitting (not shown) or the pump block 402, such as by a press-fit, detents, notches, complementary threads, or the like. In other words, the cannula 208, without the inclusion of the fitting (not shown), may be connected directly to the pump block 402.

The at least one movable pump component is the diaphragm 404 which deforms into the pump block 402 to occupy a portion of the pump volume in response to a stimulus. The stimulus may include, but is not limited to, electrical energy, thermal energy, acoustic energy, applied pressure, or electromagnetic energy. The diaphragm 404 may be composed of crystal, ceramic, polymers, plastics, metal, glass, or combinations thereof.

The diaphragm 404 and the cannula 208 may be hydraulically coupled, such that the volume from the tube end 216 of the cannula 208 and into the pump block 402 is filled with a hydraulic fluid 226. The volume from the tube end 216 of the cannula 208 and into the pump block 402 filled with the hydraulic fluid 226, which may also be referred to as a pump volume, may be contained in a substantially rigid structure, with the exception of the diaphragm 404, rather than a flexible structure, to maintain the hydraulic coupling efficiency. The hydraulic fluid 226 may be incompressible or have low compressibility. The hydraulic fluid 226 may be a solution, an oil, a liquid metal, a buffer, water, or the like. Hydraulically coupling the diaphragm 404 and the cannula 208 provides better small volume control (i.e. full piston travel draws/expels 1-50 μL) than a non-hydraulically coupled picker (i.e. filled with air). The hydraulic fluid 226 may include a fluid plug, such that two volumes of the hydraulic fluid 226 are separated by a volume of air or a different liquid. The pump volume, as seen in FIG. 4B, which is constant, satisfies the condition given by:

$$V_P = V_{HF} + V_{MPC} + V_{PM} + V_{Air},$$

where $V_P$ represents the pump volume, $V_{HF}$ represents the volume of the hydraulic fluid, $V_{MPC}$ represents the volume of the portion of the at least one movable pump component within the pump volume, where $V_{PM}$ represents the volume of any picked or aspirated material, and where $V_{Air}$ represents the volume of air within the pump volume. In this instance, the at least one moveable pump component is the diaphragm 404.

FIG. 4C shows the picker 400 with the diaphragm 404 having been driven into the pump block 402. The initial deformation distance ($d_i$) of the diaphragm 404 within the pump block 402 may be used to calculate the new volume occupied by the diaphragm 404 within the pump volume based on the shape of the diaphragm 404. The change in deformation ($\Delta d$) from the initial deformation distance to a second deformation distance ($d_s$; where $\Delta d = d_s - d_i$) may be positive (diaphragm 404 deforms into the pump block 402; and, accordingly, creates a positive pressure gradient) or negative (diaphragm 404 withdraws from the pump block 402; and, accordingly, creates a negative pressure gradient). When the pump volume is constant, the diaphragm 404 does not deform away from the pump block 402. Therefore, the furthest that the diaphragm 404 withdraws from the pump block 402 is when the diaphragm 404 sits flush with the walls of the pump block 402, as seen in FIG. 4B. It should be further noted that the dashed line in FIG. 4C denotes the neutral state of the diaphragm 404 to highlight the constant pump volume. The volume occupied by the diaphragm 404 within the pump block 402 due to the deformation of the diaphragm 404, therefore satisfies the conditions given by:

$$V_{MPC} = \frac{1}{6}\pi(d_i + \Delta d)\left(3\left(\frac{l}{2}\right)^2 + 3(d_i + \Delta d)^2\right),$$

where $V_{MPC}$ represents the at least one moveable pump component (i.e. the diaphragm 404), l represents the length of the diaphragm 404 in the picker 400 in the neutral state (as shown in FIG. 4B and represented by the dashed line in FIG. 4C), $d_i$ represents the initial deformation distance of the diaphragm 404 within the pump volume, and $\Delta d$ represents the change in deformation of the diaphragm 404 within the pump volume. With respect to the pump volume equation discussed above ($V_P = V_{HF} + V_{MPC} + V_{PM} + V_{Air}$), the pump volume remains constant because the different between the first and second volumes occupied by the at least one moveable component (i.e. diaphragm 404) is equal to the amount of the hydraulic fluid 226, picked or aspirated material, and/or air displaced from the pump volume. For example, in FIG. 4B, $d_i$ would be 0, because the diaphragm 404 sits flush with the walls of the pump block 402. However, when the diaphragm 404 deforms, as shown in FIG. 4C, the change in deformation is $\Delta d$. Now, when the diaphragm 404 deforms again (i.e. from FIG. 4C to another deformation), $d_i$ is the initial distance of deformation as shown in FIG. 4C and $\Delta d$ is any change in deformation to the new distance of deformation.

Alternatively, when a variable pump volume is desirable, the diaphragm 404 may deform away from the pump block 402. When the diaphragm 404 is able to deform away from the pump block 402, the pump volume may be variable based on the deformation of the diaphragm.

Figure 5:
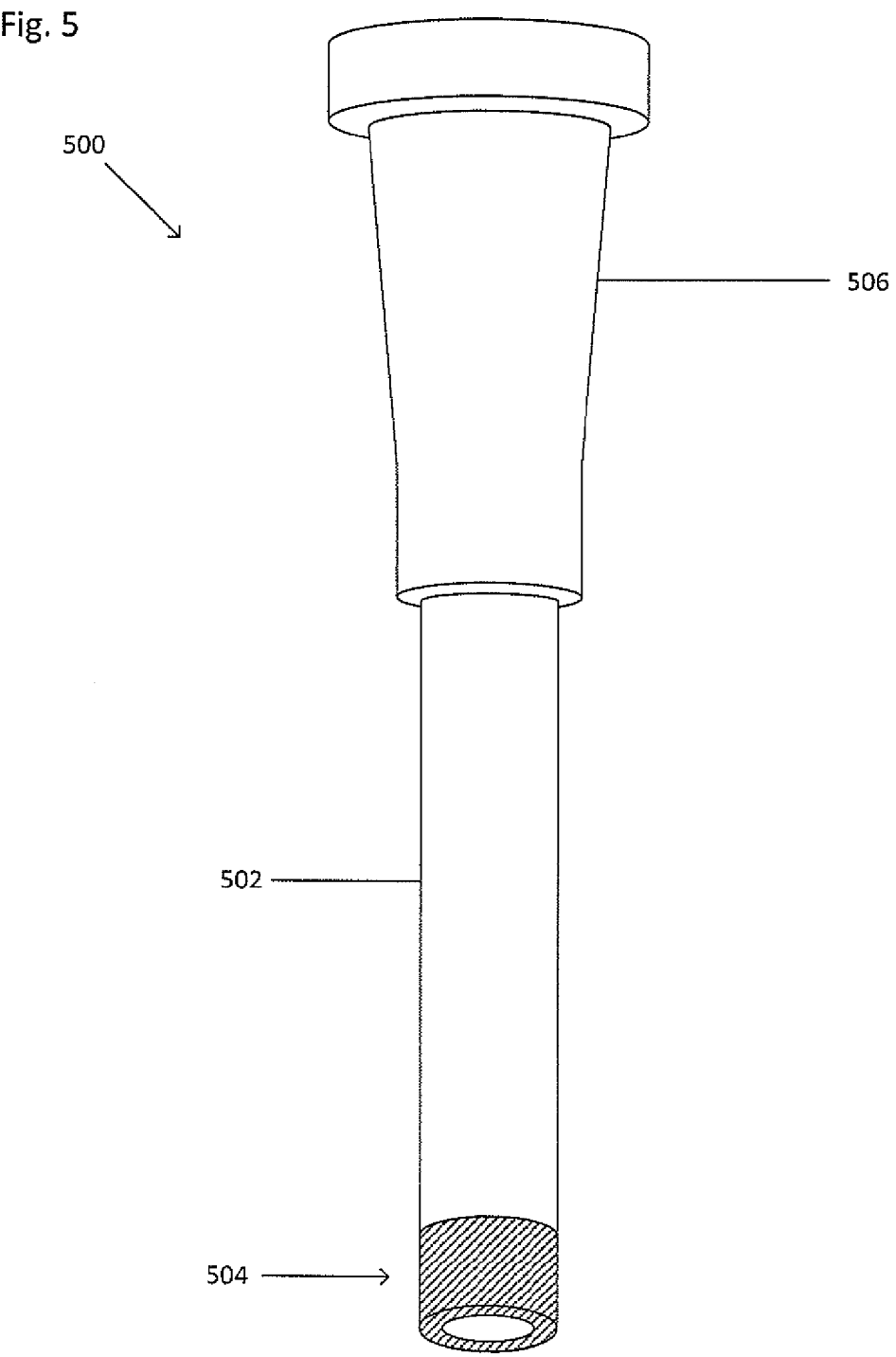
FIG. 5 shows an example cannula with a fluorescent tip.

FIG. 5 shows a cannula 500. The cannula 500 is similar to the cannula 208, except that a tube end 502 of the cannula 500 includes a fluorescent tip 504. The fluorescent tip 504 emits light in a particular wavelength when excited or stimulated by a stimulus, such as light with a first wavelength. The fluorescent tip 504 may be used to emit light that improves visualization of the cannula 500 for better placement over the desired target analyte during collection. Alternatively, the entire tube end 502 of the cannula 500 may be composed of a fluorescent material.

FIG. 6A shows a picker tip 600. FIG. 6B shows a cross-sectional view of the picker tip 600 taken along the line II-II. The picker tip 600 may be two pieces, such that the picker tip 600 may be inserted into, over, or in-line with the tube end 216 of the cannula 208. Alternatively, the picker tip 600 and the cannula 208 may be one piece. The picker tip 600 includes a main body 602 and a permeable membrane 610. The main body 602 includes a first end 604 with a first bore 612 having a first diameter and a second end 606 with a tapered bore 614 having a second diameter which tapers to the same diameter as the first diameter of the first bore 612. The second end 606 may be entirely fluorescent or a portion thereof may be fluorescent, or the second end 606 may not be fluorescent. The second diameter may be larger or smaller than the first diameter. Furthermore, the widest part of the tapered bore 614 may be less than or equal to 1 micrometer or less than or equal to 1 millimeter.

The first end 604 is inserted within the tube end 216 of the cannula 208. The permeable membrane 610 may be located within the first bore 612 or the second bore 614 and is composed of a material including at least one pore. The permeable membrane 610 permits the target analyte to be drawn a distance into the picker. The picker tip 600 may also include a ridge 608 extending circumferentially from the main body 602 to prevent the picker tip 600 from translating further into the tube end 216 of the cannula 208.

FIG. 7A shows a picker tip 700. The picker tip 700 may be inserted into, over, or in-line with the tube end 216 of the cannula 208. Alternatively, the picker tip 700 may be formed, molded, machined or the like as a single piece with the tube end 216. The picker tip 700 includes a first end 702, a second end 704, and a central bore 706. The first end 702 is the portion of the picker tip 700 which be inserted into, placed over, or placed in-line with the tube end 216 of the cannula 208. The picker tip 700 may be straight, tapered, or a combination thereof. The central bore 706 extends from the first end 702 to the second end 704 and may be straight, tapered, or a combination thereof. Furthermore, the portion of the central bore 706 at the second end 704 may be less than or equal to 1 micrometer or less than or equal to 1 millimeter.

Magnified view 708 shows the second end 704 with an outer segment removed to reveal the inner configuration of the second end 704. The second end 704 may be flat or angled. The second end 704 may also include a counter-sink, as shown in FIG. 7A.

Figure 7B:
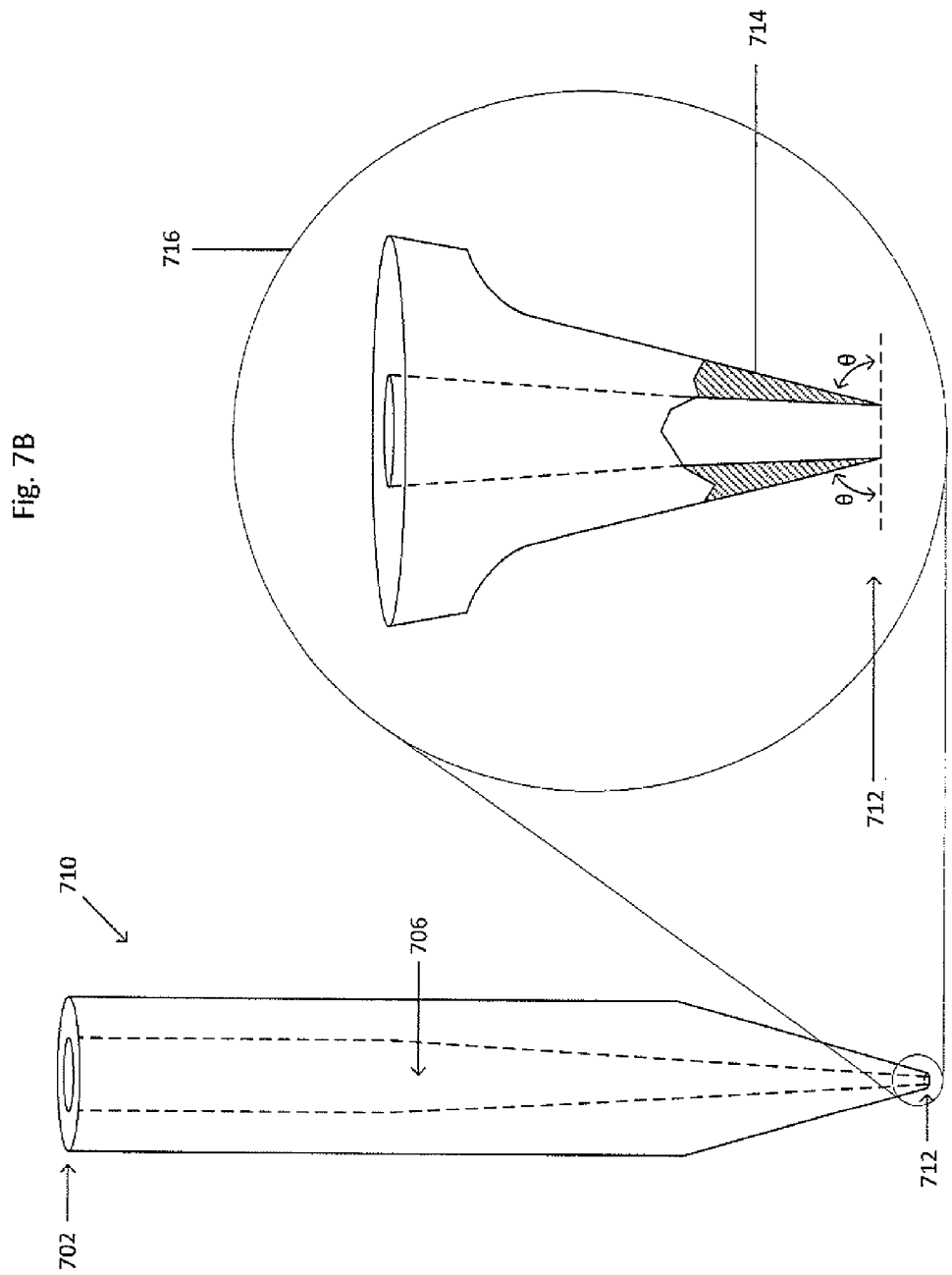

FIG. 7B shows a picker tip 710. The picker tip 710 is similar to the picker tip 700 except that the picker tip 710 includes a sharpened second end 712. Magnified view 716 shows the sharpened second end 712 having an outer wall 714 has an angle (θ) from the horizontal that may range from approximately 30° to approximately 89°. The sharpened second end 712 permits for better cutting of the desired target analyte from the substrate. The angle (θ) of the outer wall 714 permits selection of the desired target analyte without destroying any other analytes, whether target or non-target. The central bore 706 at the second end 712 may have a diameter that is less than or equal to approximately 100 micrometers.

Figure 7C:
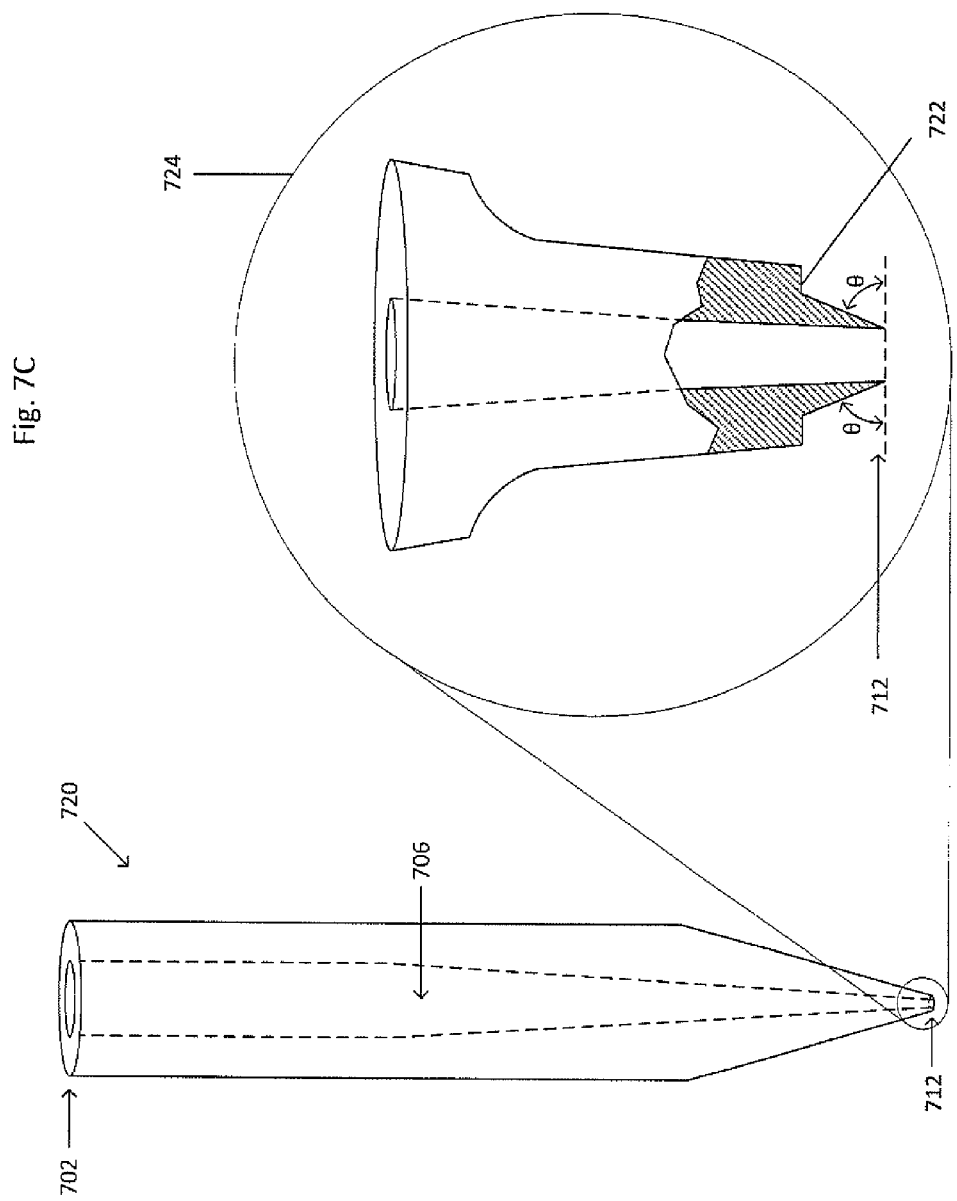

FIG. 7C shows a picker tip 720. The picker tip 720 is similar to the picker tip 710 except that the picker tip 720 includes a flat extension 722 extending from the sharpened second end 712, as seen in magnified view 724.

FIG. 7D shows a picker tip 730. The picker tip 730 is similar to the picker tip 710 except that the picker tip 730 includes a flat second end 732, as seen in magnified view 734.

Figure 7E:
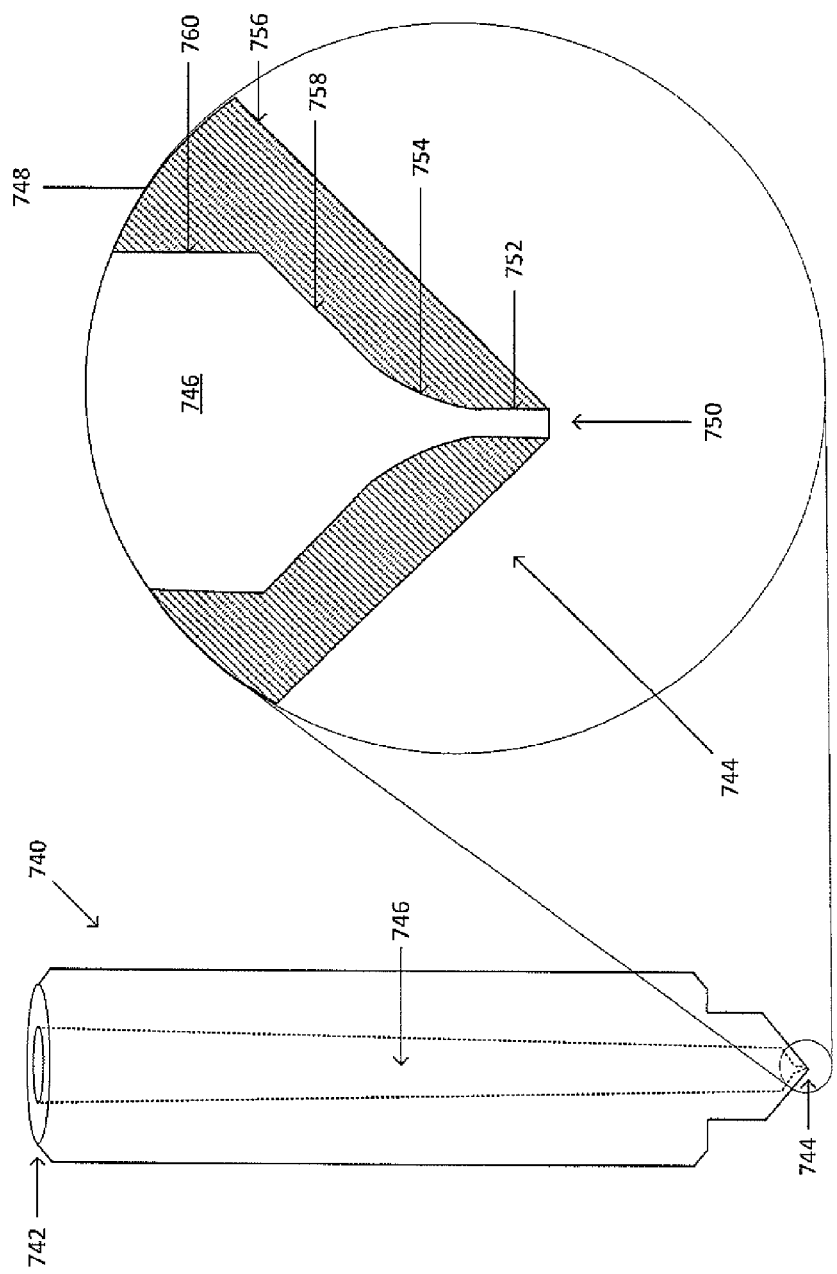

FIG. 7E shows a picker tip 740. The picker tip 740 may be inserted into, over, or in-line with the tube end 216 of the cannula 208. Alternatively, the picker tip 740 may be formed, molded, machined or the like as a single piece with the tube end 216. The picker tip 740 includes a first end 742, a second end 744, and a central bore 746. The first end 742 is the portion of the picker tip 740 which be inserted into, placed over, or placed in-line with the tube end 216 of the cannula 208. The picker tip 740 may be straight, tapered, or a combination thereof. The central bore 746 extends from the first end 742 to the second end 744 and may be straight, tapered, or a combination thereof.

Magnified view 748 shows the second end 744 with an outer segment removed to reveal the inner configuration of the second end 744. The second end 744 includes an opening 750 to access the central bore 746. An inner portion of the second end 744 includes a straight wall 752 extending from the opening 750 into the central bore. A curved wall 754 extends from the straight wall 752 further into the central bore 746. An angled wall 758 extends from the curved wall 754 further into the central bore 746. An upper wall 760 extends from the angled wall further into the central bore 746. In other words, the central bore 746 has a first diameter that is substantially equal to the diameter of the opening 750, which then increases in diameter along the curved wall 754 and the angled wall 758 until reaching the upper wall 760, whereby the diameter may remain constant or increase along a taper. The diameter of the opening 750 and the straight wall 752 may be less than or equal to 1 micrometer or less than or equal to 1 millimeter. The radius of the curved wall 754 may be approximately 25 micrometers to 2.6 millimeters. The diameter of the central bore 746 where the angled wall 758 connects to the upper wall 760 may be approximately 125 micrometers to approximately 2.6 millimeters.

The second end 744 may be sharpened, thereby having an outer wall 756 that has an angle (θ) from the horizontal that may range from approximately 30° to approximately 89°. The sharpened second end 744 permits for better cutting of the desired target analyte from the substrate. The angle (θ) of the outer wall 756 permits selection of the desired target analyte without destroying any other analytes, whether target or non-target.

FIG. 8A shows picking system 800 including a drive assembly 802, the picker 200 as shown in FIGS. 2A-2B, and an actuator 814. FIG. 8B shows a cross-sectional view of the picking system 800. Though picker 200 is described in relation to the picking system 800, the picker 230 and the picker 240 may also be used. The drive assembly 802 includes a driver 804 including a first end and second end, a coupling 624 including a first end and a second end, and a housing 806. The first end of the coupling 624 mates with the second end of the driver 804, and the second end of the coupling 624 mates with the piston 202. When the second end of the driver 804 rotates, the coupling 624 rotates, thereby causing the piston 202 to rotate and translate within the pump block 204, the fitting 206, and the cannula 208. The driver 804, the housing 806, and the coupling 624 translate with the piston 202 along the same axis, such as the z-axis, relative to the pump block 204 which remains stationary. Translation of the driver 804, the housing 806, and the coupling 624 translate with the piston 202 along the same axis reduces backlash, such as by permitting use of a single-piece coupling, to allow for better system control. The driver 804, the housing 806, the coupling 624, and the piston 202 may translate the same distance along the same axis. Alternatively, the second end of the driver 804 translates along a central axis, the coupling 624 translates along the central axis, thereby causing the piston 202 to translate within the pump block 204, the fitting 206, and the cannula 208.

The driver 804 may be an electric motor (such as a servo-motor, a stepper motor, a piezo-electric actuator, a solenoid, or the like), a manual motor (such as a knob), or the like. The driver 804 provides high resolution control of the picker 200. The coupling 624 provides zero backlash and may be axially stiff and torsionally stiff. For example, the coupling 624 may be a single piece flexure coupling, a non-expanding bellows, split-beam drive assembly, or the like.

Furthermore, backlash may be reduced by restraining or eliminating movement of the driver 804 in 5 of 6 degrees of freedom. For example, the driver 804 may translate in the z-direction, but does not translate in the x- or y-directions nor does the driver 804 rotate around the x-, y-, or z-axes. Additionally, reduced or eliminated backlash permits for greater clearance between at least the pump block 204 and the housing 806, which thereby reduces the friction between the at least two components, as well as better self-alignment of the piston 202 within the picking system 800.

The housing 806 encases and protects at least the second end of the driver 804, the coupling 624, the first end 210 of the piston 202, and at least a portion of the pump block 204. The housing 806 may inhibit rotation of the driver 804 relative to the pump block 204. The housing 806 also supports the driver 804. The housing 806 may be fixedly attached to the driver 804. The housing 806 may include a travel slot (not shown) and a screw 810, such as a shoulder screw, to set the maximum permissible travel of the pump block 204 relative to the housing 804. The screw 810 is inserted through the travel slot (not shown) and screwed into a threaded hole on a side of the pump block 204. Alternatively, the screw 810 may be inserted through the travel slot (not shown) and compressed against a side of the pump block 204.

At least one side of the pump block 204 may be biased against at least one side of the housing 806 to inhibit rotational motion between the pump block 204 and the housing 806 so as to reduce or eliminate backlash. For example, a spring (not shown) may be placed between the pump block 204 and the housing 806 below the screw head of the screw 810.

The housing 806, by supporting the driver 804 and only encasing a portion of the driver 804, may reduce or eliminate expansion of the picker 200 that may result from the heat generated by the driver 804. Decoupling or separating the picker 200 and the driver 804 may reduce or eliminate expansion of the components of the picker 100. Furthermore, the weight of the driver 804 and external constraints 622, such as springs or weights, bias and preload the threads of the piston 202 to reduce or eliminate change or backlash. When the external constraints 622 are springs, the springs may extend from the housing 806 to a base 812. When the external constraints 622 are weights, the weights may be placed on top of the driver 804 or the housing 806.

The drive assembly 802 may also include a home switch 808 to return the picker 200 to the home or original position. The drive assembly 802 may also include a driver knob 818 for manual operation and/or wire leads 620 for automated operation. Manual operation may include adjustments or movements to the picker or picking system by hand or may include motorized adjustments or movements to the picker or picking by an operator via a manual controller, such as a touch screen, a joystick, a directional pad or the like.

The picking system 800 also includes the actuator 814, such as a piezo-electric actuator, a lead screw, or a stage. The actuator 814 may be connected to the picker 200, such as by the base 812, or may be connected to the drive assembly 802. The base 812 supports the picker 200 and may connect the actuator 814 to the picker 200. The base 812 may include a light source (not shown), such as a LED, to provide epi-, transmitted, or oblique illumination of the picker tip or tube end of the cannula.

The actuator 814 provides high resolution location control of the picker 200, has a rapid response (for example, to allow for oscillation), and may be operated in an open or closed loop. The actuator 814 may provide motion along the x, y, and z axes or may provide motion along only one axis. The actuator 814 may have a travel range of 1 nanometer to more than 50 millimeters along each axis. The lower end of the travel range permits the actuator 814 to make finer adjustments (approximately 0.001-500 µm) for the picker 200 so as to better locate and pick a target analyte. The upper end of the travel range permits the actuator to make coarser adjustments (approximately 10-50 mm) for the picker 200, such as to move the picker to different wells to draw up or expel different fluids from the different wells or receptacles, to change cannulas or replace parts when it is desirous to do so. The cannula or picker tip, for example, may be replaced by manual operation (i.e. changing out by hand) or by automated operation (i.e. by expelling the used cannula or picker tip, moving the picker over a cartridge containing at least one new cannula or picker tip, lowering the picker to mate with the new cannula or picker tip, raising the picker, and returning to a desired position). When the actuator 814 provides motion along only one axis, a second actuator (not shown) may be used to provide motion along all three axes. Furthermore, when the actuator 814 provides motion along only one axis, the second actuator (not shown) may be used for coarser adjustments, whereas the actuator 814 may be used for finer adjustments.

The picking system 800 may also include a mount 816 to attach the picker 200, the drive assembly 802, and the actuator 814 to an imaging or detection system, such as a scanner or a microscope. The mount 816 may be stationary within the imaging or detection system or may be attached to the second actuator (not shown) within the imaging or detection system.

The picking system 800 may also the port 312. The port 312 may extend through the base 812, the second end of the pump block 204 and either the first end 218 of the fitting 206 or the adapter 214 of the cannula 208. The port 312 may be rigid. The port 312 may be connected to the loader 314, such as a piezoelectric pump, to fill the pump volume. The loader 314 may be connected to the reservoir 316 with the tube 318. The tube 318 may be rigid or flexible. The loader 314 may be mounted on the pump block 204, such as by a screw, adhesive, tape, or the like. The reservoir 316 may also be mounted on the pump block 204, such as by a screw, adhesive, tape, or the like; or, the reservoir 316 may be held or mounted on or within a scanning or imaging device. Alternatively, the loader 314 may be interchanged with a pressure sensor (not shown) to measure the pressure within the pump volume to make sure the picker 310 does not clog.

The picker can be composed of a variety of different materials including, but not limited to, ceramics; glass; metals; organic or inorganic materials; plastic materials; and combinations thereof. The picker tip can also be composed of a variety of different materials including, but not limited to, ceramics; glass; metals; organic or inorganic materials; plastic materials; polymers; jewels (i.e. ruby, sapphire, or diamond); and combinations thereof. Furthermore, the cannula or the picker tip may be composed of a material that is fluorescent. Additionally, the tube end of the cannula or the picker tip may be impact-resistant, hard, and dimensionally stable (i.e. axially and/or torsionally stiff). The tube end of the cannula or the picker tip may have a density that is greater than or equal to approximately 2.5 g/cc. The tube end of the cannula or the picker tip may have a hardness that is greater than or equal to approximately 80 Vickers. The tube end of the cannula or the picker tip may have a Modulus of Elasticity that is greater than or equal to approximately 65 GPa.

The permanent magnet includes, but is not limited to, a ring magnet, a bar magnet, a horseshoe magnet, a donut-shaped magnet, a spherical magnet, a polygon-shaped magnet, a polyhedral shape, a wand magnet, a kidney-shaped magnet, a trapezoidal magnet, a disk magnet, a cow magnet, a block or brick magnet, or combinations thereof. The magnetizable material includes, but is not limited to, metals, organic materials, inorganic materials, minerals, ferrofluids, and combinations thereof.

The cannula, picker tip and engagement portion may be stiff, flexible or formable. The cannula, picker tip and engagement portion may be straight, angled, curved, hooked, or any appropriate shape or configuration. The cannula, picker tip, and engagement portion may be non-clogging.

Detecting a Picker or Picking System

A picker or picking system may be used to isolate a target analyte from a suspension in or on a vessel, such as a well, a well plate, a slide, a tube, or the like, or to draw a fluid, such as a, suspension, solution or reagent, from the vessel. For example, to isolate the target analyte, the suspension suspected of containing the target analyte can be placed in the vessel. Alternatively, a fraction of the suspension, the fraction suspected of containing the target analyte, can be placed in the vessel. The vessel may be imaged to detect the target analyte and determine the location of the target analyte. After determining the location of the target analyte, an open end of the picker or picking system, such as the second end of a picking tip, the tube end of a cannula, or a tip, is guided to be located above the desired target analyte. The open end may then be moved toward the vessel until the open end eventually touches the vessel or is submerged within the suspension.

To properly determine the location of the open end, the vessel and picker or picking system may be imaged while guiding the open end into the proper position. During this imaging, the picking tip, cannula, or tip may oscillate back and forth. However, the picking tip, cannula, or tip may stop oscillating when in contact with the vessel or suspension. Therefore, by noting the point at which the oscillating terminates, the location of the picking surface may be determined and the open end may be properly visualized.

Alternatively, a sensor, such as a pressure sensor or a proximity sensor, may be placed in various locations on the imaging device, such as on a stage, in a picker or picking system component, in a turret, or the like, to detect a change in pressure or location, thereby denoting when the tip, cannula, or picking tip has contacted the picking surface.

Isolating a Target Analyte with a Picker or Picking System

A picker or picking system may be used to isolate a target analyte from a suspension. The picker or picking system may be used in conjunction with a vessel, such as a well, a well plate, a slide, or the like. For example, to isolate the target analyte, the suspension suspected of containing the target analyte can be placed in the vessel. Alternatively, a fraction of the suspension, the fraction suspected of containing the target analyte, can be placed in the vessel. The vessel may be imaged to detect the target analyte and determine the location of the target analyte. After determining the location of the target analyte, the target analyte may be isolated by the introduction of a force, such as a pressure gradient, to draw the target analyte into a picker. For example, to introduce a negative pressure gradient with the picker 200, thereby drawing the target analyte into the cannula or picker tip, the piston 202 translates away from the vessel. To introduce a positive pressure gradient with the picker 200, thereby expelling the target analyte or a releasing fluid, the piston 202 translates towards the vessel.

To remove the target analyte from a wet mount or a suspension, a negative pressure gradient may be introduced by the picker 200 after the cannula 208 is placed near, over, or above the target analyte. The negative pressure gradient causes the target analyte to move into the cannula 208.

To remove the target analyte from a dry mount (i.e. a dry slide), the cannula 208 is placed over the target analyte. The cannula 208 may then be moved horizontally or orthogonally to detach the target analyte from the mount. A negative pressure gradient may then be introduced to draw the target analyte into the cannula 208. Alternatively, the cannula 208, after being placed over the target analyte, may oscillate up and down at any appropriate frequency to detach the target analyte from the mount, such as, for example, less than or equal to approximately 10 kHz. A negative pressure gradient may then be introduced to draw the target analyte into the cannula 208. Alternatively, the cannula 208 may be placed over the target analyte and the target analyte may be held within the cannula without actively applying the pressure gradient. Alternatively, the cannula 208 may be placed over the target analyte and dragged across the surface of the slide, thereby dislodging the target analyte and causing the target analyte to be held within the cannula without actively applying the pressure gradient. Alternatively, a releasing fluid may be expelled by the cannula or picker tip by introducing a positive pressure within the picker. The releasing fluid, such as a detergent, a lysing agent, a permeabilizing agent, phosphate buffered saline, or the like, may be added on top of the desired target analyte so as to release the target analyte from the dry mount. A negative pressure gradient may then be introduced to draw the target analyte into the cannula or picker tip.

To expel the target analyte or fluid from the picker, a positive pressure gradient may be introduced by the pump. Additionally, the tube end of the cannula or the picker tip may be moved to touch the surface of the substrate onto which the target analyte or fluid is being dispense and then moved away from the surface to wick the target analyte or fluid onto the surface.

The target analyte may be collected, and once collected, the target analyte may be analyzed using any appropriate analysis method or technique, though more specifically intracellular analysis including intracellular or extracellular protein labeling; nucleic acid analysis, including, but not limited to, protein or nucleic acid microarrays; FISH; or bDNA analysis. These techniques require isolation, permeabilization, and fixation of the target analyte prior to analysis. Some of the intracellular proteins which may be labeled include, but are not limited to, cytokeratin ("CK"), actin, Arp2/3, coronin, dystrophin, FtsZ, myosin, spectrin, tubulin, collagen, cathepsin D, ALDH, PBGD, Akt1, Akt2, c-myc, caspases, survivin, $p27^{kip}$, FOXC2, BRAF, Phospho-Akt1 and 2, Phospho-Erk1/2, Erk1/2, P38 MAPK, Vimentin, ER, PgR, PI3K, pFAK, KRAS, ALKH1, Twist1, Snail1, ZEB1, Slug, Ki-67, M30, MAGEA3, phosphorylated receptor kinases, modified histones, chromatin-associated proteins, and MAGE. In order to fix, permeabilize, or label, fixing agents (such as formaldehyde, formalin, methanol, acetone, paraformaldehyde, or glutaraldehyde), detergents (such as saponin, polyoxyethylene, digitonin, octyl β-glucoside, octyl β-thioglucoside, 1-S-octyl-β-D-thioglucopyranoside, polysorbate-20, CHAPS, CHAPSO, (1,1,3,3-Tetramethylbutyl)phenyl-polyethylene glycol or octylphenol ethylene oxide), or labeling agents (such as fluorescently-labeled antibodies, Pap stain, Giemsa stain, or hematoxylin and eosin stain) may be used.

It should be understood that the method and system described and discussed herein may be used with any appropriate suspension or biological sample, such as blood, bone marrow, cystic fluid, ascites fluid, stool, semen, cerebrospinal fluid, nipple aspirate fluid, saliva, amniotic fluid, vaginal secretions, mucus membrane secretions, aqueous humor, vitreous humor, vomit, and any other physiological fluid or semi-solid. It should also be understood that a target analyte can be a cell, such as ova or a circulating tumor cell ("CTC"), a fetal cell (i.e. a trophoblast, a nucleated red blood cell, a fetal white blood cell, a fetal red blood cell, etc.), a circulating endothelial cell, an immune cell (i.e. naïve or memory B cells or naïve or memory T cells), a vesicle, a liposome, a protein, a nucleic acid, a biological molecule, a naturally occurring or artificially prepared microscopic unit having an enclosed membrane, a parasite, a microorganism, or an inflammatory cell.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

We claim:

1. A tip comprising:
   a first end;
   a second end including an outer wall having an angle from the horizontal of approximately 30° to approximately 89°; and
   a central bore extending from the first end to the second end,
   wherein the second end includes an opening to access the central bore, a straight wall extending from the opening into the central bore, a curved wall extending from the straight wall further into the central bore, an angled wall extending from the curved wall further into the central bore, and an upper wall extending from the angled wall further into the central bore.

2. The tip of claim 1, wherein the diameter of the opening and the straight is less than or equal to 1 micrometer or less than or equal to 1 millimeter.

3. The tip of claim 2, wherein the radius of the curved wall is approximately 25 micrometers to 2.6 millimeters.

4. The tip of claim 3, wherein the diameter of the central bore where the angled wall connects to the upper wall is approximately 125 micrometers to approximately 2.6 millimeters.

5. The tip of claim 4, wherein central bore maintains a constant diameter along the upper wall.

6. The tip of claim 4, wherein the central bore has an increasing diameter along the upper wall.

7. The tip of claim 1, wherein the radius of the curved wall is approximately 25 micrometers to 2.6 millimeters.

8. The tip of claim 1, wherein the diameter of the central bore where the angled wall connects to the upper wall is approximately 125 micrometers to approximately 2.6 millimeters.

9. The tip of claim 1, wherein central bore maintains a constant diameter along the upper wall.

10. The tip of claim 1, wherein the central bore has an increasing diameter along the upper wall.

11. The tip of claim 1, wherein at least the second end is composed of at least one of a ceramic, glass, a metal, an organic material, an inorganic material, a plastic material, a polymer, or a jewel.

12. The tip of claim 1, wherein at least the second end has a density that is greater than or equal to approximately 2.5 g/cc.

13. The tip of claim 12, wherein at least the second end has a hardness that is greater than or equal to approximately 80 Vickers.

14. The tip of claim 13, wherein at least the second end has a Modulus of Elasticity that is greater than or equal to approximately 65 GPa.

15. The tip of claim 1, wherein at least the second end has a hardness that is greater than or equal to approximately 80 Vickers.

16. The tip of claim 1, wherein at least the second end has a Modulus of Elasticity that is greater than or equal to approximately 65 GPa.

17. The tip of claim 1, wherein the angle of the outer wall from the horizontal is approximately 30° to approximately 80°.

18. The tip of claim 1, wherein the angle of the outer wall from the horizontal is approximately 30° to approximately 60°.

* * * * *